US011391742B2

(12) United States Patent
Vogelsang et al.

(10) Patent No.: US 11,391,742 B2
(45) Date of Patent: Jul. 19, 2022

(54) FREE HISTONE PROTEINS AS BIOMARKERS

(71) Applicant: B.R.A.H.M.S GMBH, Hennigsdorf (DE)

(72) Inventors: Maryann Stephanie Vogelsang, Natick, MA (US); Bryan Krastins, Whitingham, VT (US); Anne Incamps, Saint Victor la Coste (FR); Andre Schoenichen, Berlin (DE); Tim Ziera, Berlin (DE)

(73) Assignee: B.R.A.H.M.S. GMBH, Hennigsdorf (DE)

( * ) Notice: Subject to any disclaimer, the term of this patent is extended or adjusted under 35 U.S.C. 154(b) by 782 days.

(21) Appl. No.: 15/549,495

(22) PCT Filed: Feb. 9, 2016

(86) PCT No.: PCT/EP2016/052697
§ 371 (c)(1),
(2) Date: Aug. 8, 2017

(87) PCT Pub. No.: WO2016/128383
PCT Pub. Date: Aug. 18, 2016

(65) Prior Publication Data
US 2018/0031573 A1   Feb. 1, 2018

Related U.S. Application Data

(60) Provisional application No. 62/114,300, filed on Feb. 10, 2015.

(30) Foreign Application Priority Data

Feb. 18, 2015   (EP) .................................... 15155599

(51) Int. Cl.
*G01N 33/53* (2006.01)
*G01N 33/68* (2006.01)

(52) U.S. Cl.
CPC ..... *G01N 33/6875* (2013.01); *G01N 33/6848* (2013.01); *G01N 33/6893* (2013.01); *G01N 2800/24* (2013.01); *G01N 2800/50* (2013.01); *G01N 2800/52* (2013.01)

(58) Field of Classification Search
CPC ........... G01N 33/6875; G01N 33/6848; G01N 33/6893; G01N 2800/24; G01N 2800/50; G01N 2800/05
See application file for complete search history.

(56) References Cited

U.S. PATENT DOCUMENTS

| | | | |
|---|---|---|---|
| 10,768,182 B2 | 9/2020 | Eccleston et al. | |
| 2007/0099242 A1 | 5/2007 | Heinecke et al. | |
| 2007/0212742 A1 | 9/2007 | Bergmann et al. | |
| 2007/0239483 A1* | 10/2007 | Chandler | G06Q 40/08 705/2 |
| 2008/0003685 A1* | 1/2008 | Goix | G01N 33/582 436/86 |
| 2009/0117099 A1 | 5/2009 | Esmon et al. | |
| 2009/0221009 A1 | 9/2009 | Bergmann et al. | |
| 2010/0292131 A1 | 11/2010 | Kas et al. | |
| 2011/0008911 A1 | 1/2011 | Bergmann et al. | |
| 2014/0294843 A1 | 10/2014 | Merali et al. | |
| 2014/0322822 A1 | 10/2014 | Bergmann et al. | |
| 2017/0242037 A1 | 8/2017 | Bergmann et al. | |
| 2018/0031573 A1 | 2/2018 | Vogelsang et al. | |
| 2018/0143190 A1 | 5/2018 | Bergmann et al. | |

FOREIGN PATENT DOCUMENTS

| | | | |
|---|---|---|---|
| EP | 1488209 A1 | 12/2004 | |
| EP | 1738178 A1 | 1/2007 | |
| EP | 3256858 A1 | 12/2017 | |
| JP | H0432766 A | 2/1992 | |
| WO | 2009/062948 A1 | 5/2009 | |
| WO | 2009/097692 A1 | 8/2009 | |
| WO | 2011/029946 A1 | 3/2011 | |
| WO | WO2013103899 * | 7/2013 | ............. G01N 33/50 |
| WO | 2013191280 A1 | 12/2013 | |

OTHER PUBLICATIONS

Corada et al., Blood, 2001; 97:1679-84.*
E. A. Padlan, Adv Prot Chem 49:57-133; 1996.*
USCN ELISA Kit for Histone H4 (2009; retrieved from http://www.uscnk.com/uscn/ELISA-Kit-for-Histone-H4-(H4)-36084.htm).*
Abrams et al (Am. J. Repir Crit Care 2013,vol. 187,iss 2,pp. 160-169 ).*
Xu et al (Nat.Med 2009;15(11):1318-1321).*
Cloud Clone ELISA Kit (2009 retrieved from http://www.cloud-clone.com/products/SEA289Mi.html).*
Stemmer et al (J. Mol. Biol. (1997) 273, 52±60).*
Abrams et al Supplement (Am. J. Repir Crit Care 2013,vol. 187,iss 2,pp. 160-169, supplement.*
Lerner et al., Nature 1982; 299:592-596, see p. 595-596).*
Morita, Yoshifumi et al., "Imaging mass spectrometry of gastric carcinoma in formalin-fix paraffin-embedded tissue microarray", Cancer Science, Jan. 2010, pp. 267-273, vol. 101, No. 1.
Cretu, Daniela et al., "Identification of psoriatic arthritis mediators in synovial fluid by quantitative mass spectrometry", Clinical Proteomics, 2014, vol. 11, No. 27.

(Continued)

*Primary Examiner* — Carmencita M Belei
(74) *Attorney, Agent, or Firm* — McBee Moore & Vanik IP, LLC; Susan McBee; Chester Moore

(57) ABSTRACT

The present invention relates to method for detecting a free histone protein in a biological sample of a subject, e.g. using an immunoassay or a mass spectrometric assay. It also pertains to a method for the diagnosis, prognosis, risk assessment, risk stratification and/or therapy control of a disease or medical condition, comprising detecting a free histone protein or peptide fragment thereof in a biological sample of a subject, wherein the presence of said free histone protein or fragment thereof is indicative for said disease or medical condition.

1 Claim, 10 Drawing Sheets

Specification includes a Sequence Listing.

(56) References Cited

OTHER PUBLICATIONS

Lee, Dong-Youn et al., "Histone H4 is a Major Component of the Antimicrobial Action of Human Sebocytes", Journal of Investigative Dermatology, 2009, pp. 2489-2496, vol. 129.
Ekaney, Michael Liembo et al., "Impact of plasma histones in human sepsis and their contribution to cellular injury and inflammation", Critical Care, Biomed Central LTD., Sep. 24, 2014, p. 543, vol. 18, No. 5, London, GB.
International Search Report and Written Opinion of International Patent Application No. PCT/EP2016/052697 dated Jun. 27, 2016.
Richard D. Lane, "A short-duration polyethylene glycol fusion technique for increasing production of monoclonal antibody-secreting hybridomas," Journal of immunological methods, (1985), vol. 81, No. 2 : 223-228. [Abstract Only].

\* cited by examiner

FREE HISTONE PROTEINS AS BIOMARKERS

CROSS-REFERENCE TO RELATED APPLICATIONS

This patent application is a National Stage entry of International Patent Application No. PCT/EP2016/052697, filed Feb. 9, 2016, which claims priority to U.S. Provisional Patent Application No. 62/114,300, filed Feb. 10, 2015, and to European Patent Application No. 15155599.2, filed Feb. 18, 2015.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2905193-013001_ST25.txt" created on Jul. 24, 2017, and 19,655 bytes in size) is submitted concurrently with the instant application, and the entire contents of the Sequence Listing are incorporated herein by reference.

BACKGROUND OF THE INVENTION

The present invention relates to assays for the detection of free histone proteins and to the diagnosis of diseases or medical conditions such as systemic inflammation based on the detection of free histone proteins.

The core histone proteins H2A, H2B, H3, and H4 (two of each) form an octamer, which is wrapped by 165 base pairs of DNA to form the fundamental subunit of chromatin, the nucleosome. Each nucleosome is connected to its neighbors stabilized by the linker histones H1 and H5 (Felsenfeld G., Groudine M., Nature 2003; 421(6921): p. 448-53).

All histones share a common, compact central structure: a central helix flanked by helix-turn-helix motif. Although histone proteins are highly positively charged, their structure enables specific hydrophobic interactions with neighboring members to form a compact octamer. Regions outside the central structure described above are unstructured and contain nucleic acid interaction sides, important for formation of the nucleosome. These regions are also subject of a variety of post-translational modifications (PTMs), generally N-terminal acetylation, citrullination, methylation, and phosphorylation, as well as C-terminal ubiquitinylation. PTMs are essential for loosening nucleosome-structures, and therefore play a crucial role in various cellular processes such as gene transcription, DNA damage repair, apoptosis, as well as cell-cycle regulation (Kouzarides T., Cell 2007; 128(4): p. 693-705).

Histone proteins are also detected outside the nucleus in multiple pathophysiological processes (WO 2009/061918). The presence of extracellular histones has been described in the blood of patients suffering from different etiologies involving inflammatory processes, such as arthritis, severe trauma, pancreatitis and sepsis. Histone release from activated immune cells can be mediated by extracellular traps. Activated neutrophils, as an ultimate mechanism of controlling and clearing an infection, can release extracellular fibers, so called neutrophile extracellular traps (NETS) (Brinkmann V., et al. Science 2004; 303(5663): p. 1532-5). Other mechanisms by which histones may be released into a patient's blood stream include apoptosis, necrosis, pyroptosis or necroptosis of cells.

Once histone proteins are released into the extracellular space and enter the circulation, they unleash their pro-inflammatory and toxic potential (Xu J., et al. Nat Med 2009; 15: 1318-1321; Abrams S T., et al., J Immunol 2013; 191(5): 2495-502). Various studies revealed that circulating histone proteins not only have antimicrobial properties, but also play a pathological role in inflammatory and infectious diseases, trauma associated injuries, conditions characterized by sterile inflammation, organ damage, autoimmune diseases, cancer and retinal detachment (WO 2009/062948, U.S. Pat. No. 8,716,218, Miller B. F., et al. Science 1942; 96(2497): p. 428-430; Hirsch, J. G. J Exp Med 1958; 108(6): p. 925-44; Allam R., et al. J Mol Med 2014; 92: 465-472; Xu J., et al. Nat Med 2009; 15: 1318-1321; Abrams S T., et al., J Immunol 2013; 191(5): 2495-502; Huang H., et al. Hepatology 2011; 54: 999-1008; Kang R., et al. Gastroenterology 2014; 146: 1097-1107; Wen Z., et al. J Cell Biochem 2013; 114: 2384-2391; Xu J., et al., J Immunol 2011; 187: 2626-2631; De Meyer S F., et al. Arterioscler Thromb Vasc Biol 2012; 32: 1884-1891; Barrero C A., et al. Am J Respir Crit Care Med 2013; 188: 673-683; Allam R., et al. J Am Soc Nephrol 2012; 23: 1375-1388; Bosmann M., et al., Faseb J 2013; 27: 5010-5021; Allam R., et al., Eur J Immunol 2013; 43: 3336-3342; Kawano H., et al. Lab Invest 2014; 94: 569-585; Monach P A., et al., Proc Natl Acad Sci USA 2009; 106: 15867-15872; Hakkim A., et al., Proc Natl Acad Sci USA 2010; 107: 9813-9818; Kessenbrock K., et al., Nat Med 2009; 15: 623-625; Holdenrieder S., et al., Int J Cancer 2001; 95: 114-120).

Histone proteins might serve as biomarkers for early disease recognition and/or deterioration as well as potential therapeutic target (Chen R., et al., Cell Death and Disease 2014; 5: e1370; Xu J., et al., Nat Med 2009; 15: 1318-1321).

The lack of available and reliable quantification tools of freely circulating histones hampers the assessment of the clinical utility of these potential biomarkers.

Circulating histones in a blood-derived patients sample have been measured only indirectly by using Western Blot analysis or by determining nucleosome levels (histone octamer in association with DNA—protein DNA complex) by using Enzyme linked immunoassays (Zeerleder S., et al., Crit Care Med 2003; 31(7): p. 1947-51; Kutcher M. E., et al., J Trauma Acute Care Surg 2012; 73(6): p. 1389-94; Zeerleder S., Crit Care 2006; 10(3): p. 142; WO 2009061918). The use of Western blot analysis in clinical routine is highly questionable, due to high cost, complex technical demand and long time to results. Moreover, it requires multiple steps and is thus prone to produce subjective results. Nucleosome levels have also been detected in pathological processes. Although histone proteins reflect a fundamental part of the nucleosome, intact nucleosomes are not toxic (Abrams S T., et al., Am J Resp Crit Care Med 2013; 187: 160-169). Nucleosome assays detect histone proteins in complex with DNA. Therefore, nucleosome detection gives no information about the amount of freely circulating histones or their fragments.

Post-translational modified histone proteins can be detected by mass spectrometric techniques (Sidoli S., et al. J Proteomics 2012; 75(12): 3419-3433; Villar-Garea A., et al. Curr Protoc Protein Sci 2008; Chapter 14: Unit 14 10). The detection of histone proteins in exosomes by using Mass Spectrometry (MS) technology has been also shown for highly purified samples from in vitro cultivated tissue cultures (Buschow S. I., et al., Immunol Cell Biol 2010; 88(8): p. 851-6) or by previous gel electrophoresis (Xu J., et al., Nat Med 2009; 15: 1318-1321).

The quantitative measurement of histone proteins by using MS in native patients' plasma samples has been reported as unsuccessful due to the high abundance plasma proteins, which interfered with the detection of histone proteins. Moreover, even depletion of major abundance protein did not improve histone detectability in patients' plasma samples (Ekaney M., et al., Crit Care 2014; 18(5): p. 543).

For mass spectrometric measurements, chemical derivatization is usually performed before analyzing and quantifying the target protein (Yuan Z. F., et al., Annu Rev Anal Chem (Palo Alto Calif) 2014; 7: 113-128, Garcia B. A., et al., Nat Protoc 2007; 2(4): 933-938. WO 2013/148178). Nevertheless, no quantification method has yet been described in biological fluids without any chemical modification or labeling.

Several biomarkers for the differentiation of SIRS and sepsis have been described in the prior art (WO 2009/062948).

SUMMARY OF THE INVENTION

The present invention relates to sensitive detection methods for quantitative measurement of extracellular histone proteins in biological samples such as blood-derived samples. The herein described detection methods can target free, circulating histone proteins that are not part of a macromolecular complex such as a nucleosome or a neutrophil extracellular trap (NET). The method does not require any reduction of the complexity of the protein mixture in the sample, e.g. by initial histone protein capture through immunoprecipitation or isolation by gel electrophoresis. By analyzing the "native" sample the method of the invention avoids an inadvertent removal of histone proteins and histone derived peptides bound to non-target proteins e.g. albumin. Hence, the methods described enable a precise and standardized quantification of histone proteins by detecting histone-derived peptides in the complex native mixture of the serum and plasma proteome. Moreover the method can be applied for the clinical assessment of (critically ill) patients. The present invention relates to a method for detection of free histone proteins. This method detects for example an epitope or a peptide fragment of said histone protein which is not accessible when the histone protein is assembled in a nucleosome. In addition or alternatively, the epitope or peptide fragment of said histone protein to be detected may or may not have a post-translational modification, preferably the epitope or peptide fragment of said histone protein to be detected does not have a post-translational modification.

The methods of the present invention can be used for the diagnosis, prognosis, risk assessment, risk stratification and/or therapy control of a disease or medical condition. In the appended examples, it is demonstrated that the immunoassay and mass spectrometry based assays of the invention detect free histones in samples of subjects that suffer from a disease or medical condition; see illustrative FIGS. 1, 2 and 8.

The detection of the free histone protein or a fragment thereof can be performed using any suitable method, such as immunoassays or mass spectrometry (MS) based methods.

In particular, the present invention provides an immunoassay method for the detection of free histone proteins utilizing the methods of the invention, comprising the steps of: a) contacting the sample with a first antibody or an antigen-binding fragment or derivative thereof specific for an epitope of the free histone protein and a second antibody or an antigen-binding fragment or derivative thereof specific for an epitope of the free histone protein, and b) detecting the binding of the two antibodies or antigen-binding fragments or derivates thereof to the free histone protein.

The invention also relates to mass spectrometry (MS) based methods for the detection of free histone proteins.

The invention further relates to antibodies and kits and the use thereof in the methods of the invention.

DETAILED DESCRIPTION OF THE INVENTION

Figure 1:
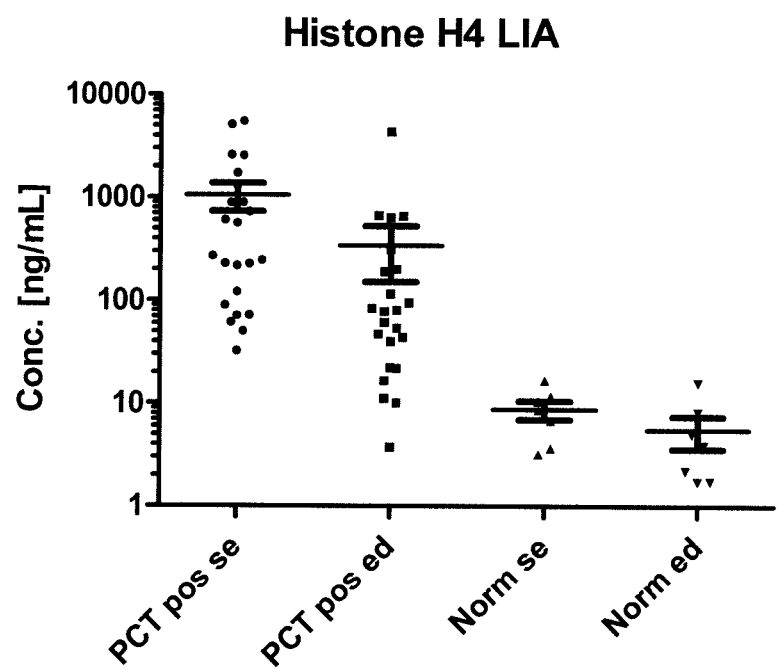
FIG. 1: Typical result of the determination of histone H4 concentrations in serum samples from healthy volunteers and samples from patients tested positive for PCT using an immunoassay.

The present invention relates to a method for detecting a free histone protein in a biological sample of a subject. The method is based on the detection of an epitope or of a peptide fragment of said histone protein.

The present invention also relates to a method for the diagnosis, prognosis, risk assessment, risk stratification and/or therapy control of a disease or medical condition, comprising detecting a free histone protein or peptide fragment thereof in a biological sample of a subject, wherein the presence of said free histone protein or fragment thereof is indicative for said disease or medical condition.

As used herein, the terms "polypeptide", "peptide", and "protein" are used interchangeably to refer to a polymer of amino acid residues.

The term "amino acid" refers to naturally occurring amino acids. Naturally occurring amino acids are those encoded by the genetic code, as well as those amino acids that are later modified, e.g., hydroxyproline, γ-carboxyglutamate, and O-phosphoserine. Amino acids may be referred to herein by either their commonly known three letter symbols or by the one-letter symbols recommended by the IUPAC-IUB Biochemical Nomenclature Commission.

Histone proteins to be detected in any of the methods of the invention encompass canonical histones as well as isoforms/variants thereof. Preferably, the free histone protein or peptide fragment thereof to be detected is selected from the group consisting of H1, H2A, H2B, H3, H4 and isoforms thereof, more preferably H2A or H4. Even more preferred, an epitope or a peptide fragment in the sequence spanning amino acid residues 20 to 55 or 70 to 118 of histone H2A according to SEQ ID NO:23 or an epitope or a peptide fragment in the sequence spanning amino acid residues 22 to 102, more preferably 46 to 102 of free histone H4 according to SEQ ID NO:1 is detected.

Histone variants as used herein are canonical or conventional variants of histones. Non-canonical (non-allelic) histones—having one or a few (up to 2, 4, 6 or 8) amino acid exchanges—are expressed at very low levels compared with their conventional counterparts. Histone variants have specific expression, localization and species-distribution patterns, and confer novel structural and functional properties on the nucleosome, affecting chromatin remodelling and histone post-translational modifications. Among the core histones, H2A has the largest number of variants, including H2A.Z, MacroH2A, H2A-Bbd, H2AvD, and H2A.X, while histone H4 is one of the slowest evolving proteins, and there appear to be no known sequence variants of histone H4.

"Free histone proteins" or "free histones" in the context of the invention encompass histone proteins which are not assembled in a macromolecular complex such as a nucleosome or a neutrophil extracellular trap (NET). Accordingly, free histones in the context of the invention are characterized that regions of said histones can be detected employing methods of the invention, which are not accessible in an assembled stoichiometric macromolecular complex, like a mononucleosome or an octamer. "Stoichiometric" in this context relates to intact complexes, e.g. a mononucleosome or an octamer. "NETs" are neutrophil extracellular traps (Brinkmann V., et al. Science 303(5663): p. 1532-5, 2004). The backbone of the NETs constitutes out of chromatin released from suicidal neutrophils and takes the form of DNA-based threads and cables. In addition to DNA, some proteins, such as histones form globular domains in these NETs. Microorganisms are killed by neutrophil cultures that have been stimulated to produce NETs. "Free histone proteins" also comprise non-chromatin-bound histones. I.e., "free histone proteins" may also comprise individual histone proteins or non-octameric histone complexes entangled in NETs. Free histone proteins are referred to as monomeric, heterodimeric or tetrameric histone proteins, which are not assembled in a ("stoichiometric") nucleosome complex consisting of the histone octamer bound to nucleic acid. Therefore, free histones are defined as individual histones present only in the form of monomers and/or homo- and heterodimers and/or homo- and heterotetramers, while bound histones are defined as histones incorporated into the octameric core of nucleosomes, consisting of two molecules each of H2A, H2B, H3 and H4 that interact via hydrophobic interactions. In the latter case central regions of the histones are covered and sterically inaccessible as these regions participate in intramolecular interactions between the individual histone molecules.

Free histones may transiently be bound to individual histones, for instance histones may form homodimers or H3 and H4, or H2A and H2B may form a heterodimer. The free histones according to the invention may also form homo- or heterotetramers. The homo- or heterotetramer consists of four molecules of histones, e.g. H2A, H2B, H3 and/or H4. A typical heterotetramer is formed by two heterodimers, wherein each heterodimer consists of H3 and H4. It is also understood herein that a heterotetramer may be formed by H2A and H2B. It is also envisaged herein that a heterotetramer may be formed by one heterodimer consisting of H3 and H4, and one heterodimer consisting of H2A and H2B. It is herein understood that the free histones can be histone variants or can be found to be associated with histone variants. In certain aspects of the invention, the free histones, e.g. a monomer, dimer or tetramer of the histone(s), are associated with nucleic acids, for example DNA. Accordingly, the antibodies and the methods of the invention can detect free histones independent of associated nucleic acids. As mentioned above, it is herein understood that the free histones are not part of the nucleosome related octamer. The octamer is the proteinaceous core particle of nucleosomes consisting of two dimers of H2A and H2B and one tetramer of H3 and H4. Example 4 documents that the immunoassay based method and the utilized antibodies thereof do not detect histones, e.g. H4, when they are part of the octameric core of nucleosomes. Similarly, the peptides detected by mass spectrometry based methods according to the invention, e.g. SEQ ID NOs: 3 and 4, originate from free histones. These detected peptides are parts of the Histone protein that would be buried and thus would be inaccessible to e.g. proteases when the histones are part of the octamer; see e.g. Example 3 and 7.

Also, free histones may transiently interact with high abundance plasma proteins including albumin, serum amyloid A, Inter-alpha Inhibitor Protein, toll-like receptors, pentraxins such as serum amyloid P and C-reactive protein driven by ionic interactions of the positively charged residues mainly at the N-terminus of the histones. Hence, free histones are still accessible by antibodies directed against central regions and the C terminus when bound to plasma proteins.

As demonstrated in the appended examples, assays, kits and antibodies are provided herein to detect free histones. For example, the free histones are detected via regions of the histones, e.g. H2A and H4, which are essentially not accessible in a stoichiometric macromolecular complex such as an octamer; see e.g. Examples 3 and 4. It is herein understood that a region of the histone is a polypeptide stretch that is accessible in a free histone, but is essentially inaccessible in case the histones are in macromolecular complexes such as an octamer. In the appended examples, methods, e.g. immunoassays as well as assays based on mass spectrometry, are demonstrated to be suitable for the detection of free histones. In particular, it is shown herein that exemplary antibodies employed in the immunoassay based method are specific for free histones. Accordingly, the antibodies of the invention have a higher binding affinity to free histones compared to bound histones found e.g. in the octamer or nucleosome. It is shown in the appended examples that said exemplary antibodies bind to regions of the histones, which are only accessible in free histones. In particular, it is proven in Example 4 that the immunoassay based methods according to the invention and the antibodies employed therein detect the free histone, e.g. H4, but do not detect said histone when it is part of the octameric core.

The free histones can also be detected employing mass spectrometric methods. As shown for the immunoassay based method, peptides can be detected by mass spectrometry, which are cleavage products of free histones; see e.g. illustrative Example 4. In other words, these peptides are generated from free histones. Without being bound by theory, the protease(s), which can be used in certain aspects of the invention to generate a proteolytic digest in preparation for mass spectrometric analysis, do(es) are not able to access the peptides of the central region when the histones are in a macromolecular complex such as an octamer. In other words, the protease can not penetrate to these cleavage sites due to sterical hindrance. Therefore, such a method detects peptides, e.g. peptide of the central regions, representing free histones.

It is demonstrated in the appended examples that the assays, kits and antibodies of the present invention detect peptides or epitopes of free histones that are accessible in free histones. These stretches of amino acids are also referred herein as central regions or parts of the histones. In the following, peptides or epitopes are described that can be employed to detect free histones using the methods herein provided. An exemplary peptide or epitope that can be employed to detect the free histone protein by the methods herein provided is an epitope or a peptide fragment in the sequence spanning amino acid residues 22 to 102 of histone H4 according to SEQ ID NO:1, or 20 to 118 of histone H2A according to SEQ ID NO:23. Furthermore, an exemplary peptide or epitope that can be employed to detect the free histone protein by the methods herein provided can be an epitope or a peptide fragment in the sequence spanning amino acid residues 27 to 62 of histone H3 according to SEQ ID NO:36, or 41 to 69 of histone H2B according to SEQ ID NO:31. More preferably, the free histone H4 is detected by the peptide(s) or epitope(s) selected from the group consisting of an amino acid sequence spanning residues 22 to 30 of SEQ ID NO:1, residues 67 to 78 of SEQ ID NO:1, residues 92 to 102 of SEQ ID NO:1, residues 22 to 34 of SEQ ID NO:1, residues 46 to 102 of SEQ ID NO:1, residues 46 to 55 of SEQ ID NO:1, residues 60 to 67 of SEQ ID NO:1, residues 80 to 91 of SEQ ID NO:1, residues 24 to 35 of SEQ ID NO:1, and residues 68 to 77 of SEQ ID NO:1.

The free histone H2A is preferably detected by the peptide(s) or epitope(s) selected from the group consisting of an amino acid sequence spanning residues 21 to 53 of SEQ ID NO:23, residues 21 to 29 of SEQ ID NO:23, residues 30 to 53 of SEQ ID NO:23, residues 120 to 129 of SEQ ID NO: 23, residues 21 to 29 of SEQ ID NO: 23, residues 82 to 88 of SEQ ID NO: 23, residues 89 to 95 of SEQ ID NO: 23, and residues 100 to 118 of SEQ ID NO: 23.

The free histone H2B is preferably detected by the peptide or epitope spanning residues 41 to 69 of SEQ ID NO: 31.

The free histone H3 is preferably detected by the peptide(s) or epitope(s) spanning from residues 27 to 37 of SEQ ID NO: 36 and/or spanning residues 52 to 62 of SEQ ID NO: 36.

As used herein, the term "chromatin" refers to the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. A "chromosome" is a chromatin complex comprising all or a portion of the genome of a cell.

Herein, the term "nucleosome" or "nucleosome complex" means the fundamental unit of chromatin which is composed of an octamer of the four core histones H3, H4, H2A and H2B around which approximately 150 base pairs of DNA are wrapped.

The epitope detected may preferably be an epitope which is not accessible when the histone is assembled in a nucleosome. As described above, "not accessible" in the context of the invention means that the epitope cannot be specifically bound by a ligand, particularly by an antibody, when the histone is part of a nucleosome complex. Also encompassed are epitopes which are not structurally accessible due to steric hindrance when the histone is part of the nucleosome complex.

The term "fragment" in the context of the invention refers to smaller proteins or peptides derivable from larger proteins or peptides, which hence comprise a partial sequence of the larger protein or peptide. Said fragments are derivable from the larger proteins or peptides by hydrolysis of one or more of its peptide bonds. The fragments preferably have at least 6, 9, 10 or 12 residues.

Herein, the term "sample" is a biological sample. "Sample" as used herein may, e.g., refer to a sample of bodily fluid or tissue obtained for the purpose of diagnosis, prognosis, or evaluation of a subject of interest, such as a patient.

Preferably herein, the sample is a sample of a bodily fluid or a tissue of the subject. A bodily fluid sample is preferred. Preferred test samples include blood, serum, plasma, cerebrospinal fluid, urine, saliva, sputum, and pleural effusions. In addition, one of skill in the art would realize that some test samples would be more readily analyzed following a fractionation or purification procedure, for example, separation of whole blood into serum or plasma components.

Thus, preferably the sample used in the present invention is selected from the group consisting of a blood sample, a serum sample, a plasma sample, a cerebrospinal fluid sample, a saliva sample, a urine sample, a tissue sample or an extract of any of the aforementioned samples.

Preferably, the sample is a blood sample, more preferably a serum sample or a plasma sample. Serum samples are the most preferred samples in the context of the present invention.

Where appropriate, the sample can be homogenized, or extracted with a solvent prior to use in the present invention in order to obtain a liquid sample. A liquid sample hereby may be a solution or suspension. Liquid samples may be subjected to one or more pre-treatments prior to use in the present invention. Such pre-treatments include, but are not limited to dilution, filtration, centrifugation, concentration, sedimentation, precipitation or dialysis. Pre-treatments may also include the addition of chemical or biochemical substances to the solution, such as acids, bases, buffers, salts, solvents, reactive dyes, detergents, emulsifiers, chelators.

"Plasma" in the context of the present invention is the virtually cell-free supernatant of blood containing anticoagulant obtained after centrifugation. Exemplary anticoagulants include calcium ion binding compounds such as EDTA or citrate and thrombin inhibitors such as heparinates or hirudin. Cell-free plasma can be obtained by centrifugation of the anticoagulated blood (e.g. citrated, EDTA or heparinized blood), for example for at least 15 minutes at 2000 to 3000 g.

"Serum" in the context of the present invention is the liquid fraction of whole blood that is collected after the blood is allowed to clot. When coagulated blood (clotted blood) is centrifuged serum can be obtained as supernatant.

The terms "patient", "individual" and "subject" may be used interchangeably throughout the present invention. A "patient", "individual" or "subject" for the purposes of the present invention includes both humans and other animals, particularly mammals, and other organisms. Thus, the methods are applicable to both human diagnostics and veterinary applications. In a preferred embodiment the patient is a mammal, and in the most preferred embodiment the patient or subject is a human. The term "patient" as used herein refers to a living human or non-human organism that is not receiving medical care or is receiving medical care or that should receive medical care due to a disease or medical condition, particularly systemic inflammation. This includes persons with no defined illness who are being investigated for signs of pathology. Thus the methods and assays described herein are applicable to both, human and veterinary disease.

The term "epitope", also known as antigenic determinant, used herein refers to the part of an antigen that is recognized by antibodies, B cells, or T cells. Accordingly, "epitope" means a portion of a molecule to which an antibody binds, e.g. a polypeptide stretch. Both conformational epitopes and linear epitopes are encompassed by the term "epitope".

In the context of the present invention, the free histone protein or peptide fragment thereof detected in a method of the present invention can be seen as a biomarker. The term "biomarker" (biological marker) relates to measurable and quantifiable biological parameters (e.g., specific enzyme concentration, specific hormone concentration, specific gene phenotype distribution in a population, presence of biological substances) which serve as indices for health- and physiology-related assessments, such as disease risk, psychiatric disorders, environmental exposure and its effects, disease diagnosis, metabolic processes, substance abuse, pregnancy, cell line development, epidemiologic studies, etc. Furthermore, a biomarker is defined as a characteristic that is objectively measured and evaluated as an indicator of normal biological processes, pathogenic processes, or pharmacologic responses to a therapeutic intervention. A biomarker may be measured on a biological sample (as a blood, urine, or tissue test), it may be a recording obtained from a person (blood pressure, ECG, or Holter). Biomarkers can indicate a variety of health or disease characteristics, including the level or type of exposure to an environmental factor, genetic susceptibility, genetic responses to exposures, biomarkers of subclinical or clinical disease, or indicators of response to therapy. Thus, a simplistic way to think of biomarkers is as indicators of disease trait (risk factor or risk biomarker), disease state (preclinical or clinical), or disease rate (progression). Accordingly, biomarkers can be classified as antecedent biomarkers (identifying the risk of developing an illness), screening biomarkers (screening for subclinical disease), diagnostic biomarkers (recognizing overt disease), staging biomarkers (categorizing disease severity), or prognostic biomarkers (predicting future disease course, including recurrence and response to therapy, and monitoring efficacy of therapy). Biomarkers may also serve as surrogate end points. A surrogate end point is one that can be used as an outcome in clinical trials to evaluate safety and effectiveness of therapies in lieu of measurement of the true outcome of interest. The underlying principle is that alterations in the surrogate end point track closely with changes in the outcome of interest. Surrogate end points have the advantage that they may be gathered in a shorter time frame and with less expense than end points such as morbidity and mortality, which require large clinical trials for evaluation. Additional values of surrogate end points include the fact that they are closer to the exposure/intervention of interest and may be easier to relate causally than more distant clinical events. An important disadvantage of surrogate end points is that if clinical outcome of interest is influenced by numerous factors (in addition to the surrogate end point), residual confounding may reduce the validity of the surrogate end point. It has been suggested that the validity of a surrogate end point is greater if it can explain at least 50% of the effect of an exposure or intervention on the outcome of interest. For instance, a biomarker may be a protein, peptide or a nucleic acid molecule. The free histone proteins may in the context of the present invention be used together with other biomarkers, i.e. the free histone proteins may be part of a biomarker panel.

"Diagnosis" in the context of the present invention relates to the recognition and (early) detection of a disease or clinical condition in a subject and may also comprise differential diagnosis. Also the assessment of the severity of a disease or clinical condition may in certain embodiments be encompassed by the term "diagnosis".

"Prognosis" relates to the prediction of an outcome or a specific risk for a subject suffering from a particular disease or clinical condition. This may include an estimation of the chance of recovery or the chance of an adverse outcome for said subject.

The methods of the invention may also be used for monitoring. "Monitoring" relates to keeping track of an already diagnosed disease, disorder, complication or risk, e.g. to analyze the progression of the disease or the influence of a particular treatment on the progression of disease or disorder.

The term "therapy control" in the context of the present invention refers to the monitoring and/or adjustment of a therapeutic treatment of said patient.

In the present invention, the terms "risk assessment" and "risk stratification" relate to the grouping of subjects into different risk groups according to their further prognosis. Risk assessment also relates to stratification for applying preventive and/or therapeutic measures.

In addition or alternatively, in the methods of the invention, the epitope or peptide fragment of said free histone protein to be detected does not have a post-translational modification.

The term "post-translational modifications" or "PTMs" in the context of the present invention refer to modifications that occur on a protein, catalyzed by enzymes, after its translation by ribosomes is complete. Post-translational modification generally refers to the addition of a functional group covalently to a protein. Preferably, "post-translational modifications" of histones in the context of the invention are modifications, which are, for example, introduced by acetyltransferases, lysine methyltransferases and lysine demethylases. Preferably a post-translational modification in the context of the present invention is selected from the group consisting of acetylation, citrullination, deacetylation, methylation, demethylation, deimination, isomerization, phosphorylation and ubiquitination.

In the context of the diagnostic, prognostic and risk assessment methods of the present invention, at least one clinical parameter can additionally be analyzed, whereby the clinical parameter are selected from the group comprising body temperature, blood pressure, heart rate, leukocyte value.

In the context of the diagnostic, prognostic and risk assessment methods of the present invention, at least one biomarker can additionally be analyzed, whereby the biomarker is selected from the group comprising Calcitonin, Adrenomedullin (ADM/proADM), Endothelin-1 (ET-1), Arginine Vasopressin (AVP), Atrial Natriuretic Peptide (ANP), Neutrophil Gelatinase-Associated Lipocalin (NGAL), Troponin, Brain Natriuretic Peptide (BNP), C-Reactive Protein (CRP), Pancreatic Stone Protein (PSP), Triggering Receptor Expressed on Myeloid Cells 1 (TREM1), Interleukin-6 (IL-6), Interleukin-20 (IL-20), Interleukin-22 (IL-22), Interleukin-24 (IL-24) other ILs, Presepsin, Lipopolysaccharide Binding Protein (LBP), Alpha-1-Antitrypsin, Matrix Metalloproteinase 2 (MMP2), Matrix Metalloproteinase 9 (MMP9) and Tumor Necrosis Factor α (TNFα). Preferably at least one biomarker selected from the group comprising Procalcitonin (PCT), Adrenomedulin (ADM/proADM), Presepsin (sCD14-ST), and C reactive Protein (CRP).

The disease or medical condition of any of the methods of the invention may be selected from diseases or medical conditions that involve the systemic inflammatory response (SIRS) of an individual related to infective and non-infective etiologies such as sepsis, severe sepsis and septic shock caused by microbial stimuli i.e. bacteria, viruses, fungi and/or parasites, traumatic injury and/or hemorrhage, ischemia reperfusion injury, burn injuries, acute pancreatitis as well as interventional procedures such as e.g. cardio-pulmonary bypass, chemotherapy and radiotherapy where an individual is at risk of developing, endothelial tissue damage, thromboembolism and acute disseminated intravascular coagulation (DIC), contributing to single or multiple organ dysfunction and failure (in particular acute kidney injury, acute lung injury and liver injury) during the course of the disease.

"Systematic inflammation" in the context of the invention preferably relates to a condition characterized by a release of pro-inflammatory cytokines and an activated innate immune system which can be caused by biological factors, chemical factors or by genetic factors. Severe "Systemic Inflammation" can lead to organ failure and death.

"SIRS" in the context of the invention is a systemic inflammatory response syndrome with no signs of infection. It includes, but is not limited to more than one of the following clinical manifestations: (1) a body temperature greater than 38° C. or less than 36° C.; (2) a heart rate greater than 90 beats per minute; (3) tachypnea, manifested by a respiratory rate greater than 20 breaths per minute, or hyperventilation, as indicated by a $PaCO_2$ of less than 32 mm Hg; and (4) an alteration in the white blood cell count such as a count greater than 12,000/mm$^3$, a count less than 4,000/mm$^3$, or the presence of more than 10% immature neutrophiles (Bone et al., CHEST 101(6): 1644-55, 1992).

"Sepsis" in the context of the invention means the systemic response to infection. Alternatively, sepsis may be seen as the combination of SIRS with a confirmed infectious process. Sepsis may be characterized as clinical syndrome defined by the presence of both infection and a systemic inflammatory response (Levy M M et al. 2001 SCCM/ESICM/ACCP/ATS/SIS International Sepsis Definitions Conference. Crit Care Med. 2003 April; 31(4):1250-6). The term "sepsis" used herein includes, but is not limited to, sepsis, severe sepsis, septic shock. Severe sepsis in this context means sepsis associated with organ dysfunction, hypoperfusion abnormality, or sepsis-induced hypotension. Hypoperfusion abnormalities include lactic acidosis, oliguria and acute alteration of mental status. Sepsis-induced hypotension is defined by the presence of a systolic blood pressure of less than 90 mm Hg or its reduction by 40 mm Hg or more from baseline in the absence of other causes for hypotension (e.g. cardiogenic shock). Septic shock is defined as severe sepsis with sepsis-induced hypotension persisting despite adequate fluid resuscitation, along with the presence of hypoperfusion abnormalities or organ dysfunction (Bone et al., CHEST 101(6): 1644-55, 1992). The term "sepsis" used herein relates to all possible stages in the development of sepsis.

The aforementioned "infection" within the scope of the invention means a pathological process caused by the invasion of normally sterile tissue or fluid by pathogenic or potentially pathogenic microorganisms and relates to infections by bacteria, fungi, parasites and/or viruses.

"Pancreatitis" in the context of the invention may be seen as inflammation of the pancreas that progresses from acute (sudden onset; duration 6 months) to recurrent acute (>1 episode of acute pancreatitis) to chronic (duration >6 months). Within the scope of the invention, but not limited to, are familiar pancreatitis, hereditary pancreatitis and Idiopathic sporadic pancreatitis.

The term "polytrauma" or "multitrauma" in the context of the invention encompasses a condition with two or more severe injuries in at least two areas of the body or a condition with a multiple injury, i.e. two or more severe injuries in one body area. Polytrauma may be accompanied with traumatic shock and/or hemorrhagic hypotension and a serious endangering of one or more vital functions. At least one out of two or more injuries or the sum total of all injuries endangers the life of the injured subject with polytrauma (Kroupa J., Acta Chir Orthop Traumatol Cech. 1990 July;57(4):347-60). In the context of the present invention the disease or condition is preferably systemic inflammation, more preferably sepsis or SIRS.

As mentioned above, the free histone proteins may be detected using any suitable method. Immunoassay-based methods and mass spectrometry-based methods are particularly preferred in the context of the present invention and will be described in more detail in the following:

Immunoassay Based-Methods

The invention further relates to an immunoassay utilizing any of the methods of the invention. In particular, the immunoassay method comprises the steps of a) contacting the sample with a first antibody or an antigen-binding fragment or derivative thereof specific for a first epitope of the free histone protein target and a second antibody or an antigen-binding fragment or derivative thereof specific for a second epitope of the free histone protein target, and b) detecting the binding of the two antibodies or antigen-binding fragments or derivates thereof to the free histone protein. One example of such an assay is a sandwich ELISA assay.

Herein, the term "antibody" also comprises antigen-binding fragments or derivatives unless otherwise stated.

Alternatively, instead of antibodies, other capture molecules or molecular scaffolds that specifically and/or selectively recognize histone sequences, histone epitopes, and structural conformations of histones may be encompassed by the scope of the present invention.

Herein, the term "capture molecules" or "molecular scaffolds" comprises molecules which may be used to bind target molecules or molecules of interest, i.e. analytes (i.e. in the context of the present invention free histone protein), from a sample. Capture molecules must thus be shaped adequately, both spatially and in terms of surface features, such as surface charge, hydrophobicity, hydrophilicity, presence or absence of lewis donors and/or acceptors, to specifically bind the target molecules or molecules of interest. Hereby, the binding may for instance be mediated by ionic, van-der-Waals, pi-pi, sigma-pi, hydrophobic or hydrogen bond interactions or a combination of two or more of the aforementioned interactions or covalent interactions between the capture molecules or molecular scaffold and the target molecules or molecules of interest. In the context of the present invention, capture molecules or molecular scaffolds may for instance be selected from the group consisting of a nucleic acid molecule, a carbohydrate molecule, a PNA molecule, a protein, a peptide and a glycoprotein. Capture molecules or molecular scaffolds include, for example, aptamers, DARpins (Designed Ankyrin Repeat Proteins). Affimers and the like.

The term "antibody" generally comprises monoclonal, genetically engineered monoclonal antibodies, and polyclonal antibodies and binding fragments thereof, in particular Fc-fragments as well as so called "single-chain-antibodies" (Bird R. E. et al (1988) Science 242:423-6), chimeric, humanized, in particular CDR-grafted antibodies, and diabodies or tetrabodies (Holliger P. et al (1993) Proc. Natl. Acad. Sci. U.S.A. 90:6444-8). Antibodies can be both naturally occurring and non-naturally occurring. Furthermore, antibodies include wholly synthetic antibodies, single chain antibodies, and fragments thereof. Antibodies may be human or nonhuman. Nonhuman antibodies may be humanized by recombinant methods to reduce their immunogenicity in humans. Antibody fragments include, without limitation, Fab and Fc fragments. The "Fc portion of an antibody", can be a crystallizable fragment obtained by papain digestion of immunoglobulin that consists of the C-terminal half of two heavy chains linked by disulfide bonds and known as the "effector region" of the immunoglobulin. "Fc portion of an antibody" may also mean all, or substantially all, of one C-terminal half of a heavy chain. Also comprised are immunoglobulin-like proteins that are selected through techniques including, for example, phage display to specifically bind to the molecule of interest contained in a sample. In this context the terms "specific" and "specific binding" refer to antibodies raised against the molecule of interest or a fragment thereof. An antibody is considered to be specific, if its affinity towards the molecule of interest (here: free histone proteins) or the aforementioned fragment thereof is at least 50-fold higher, preferably 100-fold higher, most preferably at least 1000-fold higher than towards other molecules comprised in a sample containing the molecule of interest. It is well known in the art how to develop and to select antibodies with a given specificity. In the context of the invention, monoclonal antibodies are preferred.

As will be discussed herein below in more detail the (first and/or second) antibodies or antigen-binding fragments or derivatives thereof of the invention may for instance be polyclonal antibodies, monoclonal antibodies or genetically engineered monoclonal antibodies.

The binding of the antibodies to a free histone protein (or a fragment thereof) takes place under suitable conditions (i.e. allowing for immunoreactions, i.e. binding of the antibodies to a free histone protein and formation of immune complexes). Such conditions are known to the skilled person and standard formats of immunoassays e.g. as described below can be used. Such conditions will preferably be under physiologic temperature, pH and ionic strength and can take place in media such as, for example, phosphate buffered saline (PBS).

In the illustrative Examples 1 to 4, antibodies and immunoassay based methods are described to detect free histones. It is demonstrated in the appended examples that an epitope to detect the free histone protein can be an epitope present in the sequence spanning amino acid residues 22 to 102 of histone H4 according to SEQ ID NO:1, or 20 to 118 of histone H2A according to SEQ ID NO:23. Furthermore, an epitope to detect the free histone protein can be an epitope present in the sequence spanning amino acid residues 27 to 62 of histone H3 according to SEQ ID NO:36, or 41 to 69 of histone H2B according to SEQ ID NO:31.

Furthermore, the immunoassay methods of the present invention may preferably utilize a first antibody and/or a second antibody or antigen-binding fragment(s) or derivative(s) thereof being specific for (an) epitope(s) of a free histone H4, wherein the first epitope and/or second epitope are epitopes of histone H4 present in the sequence spanning amino acid residues 22 to 102 of SEQ ID NO:1.

Furthermore, the immunoassay methods of the present invention may utilize a first antibody and/or a second antibody or antigen-binding fragment(s) or derivative(s) thereof being specific for (an) epitope(s) of a free histone H2A, wherein the first epitope and/or second epitope are epitopes of histone H2A present in the sequence spanning amino acid residues 21 to 53, 20 to 118 or 120 to 129 of SEQ ID NO:23.

Furthermore, the immunoassay methods of the present invention may utilize a first antibody and/or a second antibody or antigen-binding fragment(s) or derivative(s) thereof being specific for (an) epitope(s) of a free histone H3, wherein the first epitope and/or second epitope are epitopes of histone H3 present in the sequence spanning amino acid residues 27 to 63 of SEQ ID NO:36.

More preferably, the immunoassay methods of the present invention utilize a first antibody and/or a second antibody or antigen-binding fragment(s) or derivative(s) thereof being specific for (an) epitope(s) of a free histone H4, wherein the epitope(s) is/are selected from the group consisting of an amino acid sequence spanning residues 22 to 30 of SEQ ID NO:1, residues 67 to 78 of SEQ ID NO:1, residues 92 to 102 of SEQ ID NO:1, residues 22 to 34 of SEQ ID NO: 1, and residues 46 to 102 of SEQ ID NO: 1.

Furthermore, the immunoassay methods of the present invention preferably utilize a first antibody and/or a second antibody or antigen-binding fragment(s) or derivative(s) thereof being specific for (an) epitope(s) of a free histone H2A, wherein the epitope(s) is/are selected from the group consisting of an amino acid sequence spanning residues 21 to 53 of SEQ ID NO:23, residues 21 to 29 of SEQ ID NO:23, residues 30 to 53 of SEQ ID NO:23, and residues 120 to 129 of SEQ ID NO: 23.

Furthermore, the immunoassay methods of the present invention may utilize a first antibody and/or a second antibody or antigen-binding fragment(s) or derivative(s) thereof being specific for (an) epitope(s) of a free histone H2B spanning residues 41 to 69 of SEQ ID NO: 31.

Furthermore, the immunoassay methods of the present invention may utilize a first antibody and/or a second antibody or antigen-binding fragment(s) or derivative(s) thereof being specific for (an) epitope(s) of a free histone H3 spanning residues 27 to 37 of SEQ ID NO: 36 and/or spanning residues 52 to 62 of SEQ ID NO: 36.

Furthermore, the immunoassay methods of the present invention preferably utilize a first antibody and/or the second antibody or the antigen-binding fragment(s) or derivative(s) thereof being specific for (an) epitope(s) of a free histone H2A present in the sequence spanning amino acid residues 21 to 53 and/or 120 to 129 of the histone H2A sequence represented by SEQ ID NO:23. In other words, the immunoassay methods of the present invention preferably may utilize a first antibody and/or the second antibody or the antigen-binding fragment or derivative thereof which are specific for an epitope of histone H2A present in the sequence spanning amino acid residues 21 to 53 and/or 120 to 129 of the histone H2A sequence represented by SEQ ID NO:23.

Furthermore, the immunoassay methods of the present invention may utilize a first antibody, antigen-binding fragment or derivative thereof that is specific for an epitope of histone H4 present in the sequence spanning amino acid residues 22 to 102 of SEQ ID NO:1, and a second antibody, antigen-binding fragment or derivative thereof that is specific for an epitope of a free histone H2A, H2B, or preferably H3.

Furthermore, the immunoassay methods of the present invention may utilize a first antibody, antigen-binding fragment or derivative thereof that is specific for an epitope of histone H2A present in the sequence spanning amino acid residues 21 to 53, 120 to 129, or 20 to 118 of SEQ ID NO:23, and a second antibody, antigen-binding fragment or derivative thereof that is specific for an epitope of a free histone H3, H4 or preferably H2B.

Furthermore, the immunoassay methods of the present invention may utilize a first antibody, antigen-binding fragment or derivative thereof that is specific for an epitope of histone H3 present in the sequence spanning amino acid residues 27 to 62 of SEQ ID NO:36, and a second antibody, antigen-binding fragment or derivative thereof that is specific for an epitope of a free histone H4, or preferably H2A, or H2B.

It is herein understood that, in the context of the immunoassay methods provided herein, the order of the contacting steps in relation to the "first" and the "second" antibody, antigen-binding fragment or derivative thereof can be changed. Thus, it is herein understood that first the "second" antibody, antigen-binding fragment or derivative thereof can be contacted with the sample and subsequently the "first" antibody, antigen-binding fragment or derivative thereof can be contacted with the sample. It is also herein understood that the two antibodies, antigen-binding fragments or derivatives thereof can be contacted with the sample simultaneously.

The immunoassay methods of the present invention may utilize a first antibody or the antigen-binding fragment or derivative thereof which is specific for an epitope of histone H2A present in the sequence spanning amino acid residues 21 to 29 of SEQ ID NO:23 and/or the second antibody or the antigen-binding fragment or derivative thereof which is specific for an epitope of histone H2A present in the sequence spanning amino acid residues 30 to 53 of SEQ ID NO:23.

The immunoassay methods of the present invention preferably may also utilize a first antibody or the antigen-binding fragment or derivative thereof which is specific for an epitope of histone H4 present in the sequence spanning amino acid residues 22 to 30 SEQ ID NO:1 (corresponding to peptide H4-LI-9, SEQ ID NO:10) or residues 46 to 102 of SEQ ID NO:1 (corresponding to SEQ ID NO:2) or residues 22 to 34 of SEQ ID NO:1 and a second antibody or the antigen-binding fragment or derivative thereof which is specific for an epitope in the sequence spanning amino acid residues 46 to 102 of histone H4 (SEQ ID NO:1).

The immunoassay methods of the present invention may utilize a first antibody or the antigen-binding fragment or derivative thereof which is specific for an epitope of histone H4 present in the sequence spanning amino acid residues 20 to 30 of SEQ ID NO:1 or residues 67 to 78 of SEQ ID NO:1 or residues 92 to 102 of SEQ ID NO:1 or residues 22 to 34 of SEQ ID NO:1, preferably residues 67 to 78 of SEQ ID NO:1 and/or the second antibody or the antigen-binding fragment or derivative thereof which is specific for an epitope of histone H4 present in the sequence spanning amino acid residues 46 to 102 of SEQ ID NO:1.

The preferred detection methods comprise immunoassays in various formats such as for instance radioimmunoassay (RIA), chemiluminescence- and fluorescence-immunoassays, enzyme immunoassay (EIA), Enzyme-linked immunoassays (ELISA), Luminescence-based bead arrays, magnetic beads based assay, protein microarray assays, rapid test formats such as for instance immunochromatographic strip tests.

The assays of the invention can be homogenous or heterogeneous assays, competitive and non-competitive assays. In a particularly preferred embodiment, the assay is in the form of a sandwich assay, which is a non-competitive immunoassay, wherein the molecule to be detected and/or quantified is bound to a first antibody and to a second antibody. The first antibody may be bound to a solid phase, e.g. a bead, a surface of a well or other container, a chip or a strip, and the second antibody is an antibody which is labeled, e.g. with a dye, with a radioisotope, or a reactive or catalytically active moiety or vice versa. The amount of labeled antibody bound to the analyte is then measured by an appropriate method. The general composition and procedures involved with "sandwich assays" are well-established and known to the skilled person (The Immunoassay Handbook, Ed. David Wild, Elsevier LTD, Oxford; 3rd ed. (May 2005), ISBN-13: 978-0080445267; Hultschig C et al., Curr Opin Chem Biol. 2006 February;10(1):4-10. PMID: 16376134, incorporated herein by reference).

In the context of the invention, the assay may comprise two capture molecules, preferably antibodies which are both present as dispersions in a liquid reaction mixture, wherein a first labelling component is attached to the first capture molecule, wherein said first labelling component is part of a labelling system based on fluorescence- or chemiluminescence-quenching or amplification, and a second labelling component of said marking system is attached to the second capture molecule, so that upon binding of both capture molecules to the analyte a measurable signal is generated that allows for the detection of the formed sandwich complexes in the solution comprising the sample.

Preferably, said labelling system comprises rare earth cryptates or rare earth chelates in combination with fluorescence dye or chemiluminescence dye, in particular a dye of the cyanine type.

In the context of the present invention, fluorescence based assays may comprise the use of dyes, which may for instance be selected from the group comprising FAM (5- or 6-carboxyfluorescein), VIC, NED, Fluorescein, Fluorescein-isothiocyanate (FITC), IRD-700/800, Cyanine dyes, such as CY3, CY5, CY3.5, CY5.5, Cy7, Xanthen, 6-Carboxy-2',4', 7',4,7-hexachlorofluorescein (HEX), TET, 6-Carboxy-4',5'-dichloro-2',7'-dimethodyfluorescein (JOE), N,N, N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), Rhodamine, Rhodamine Green, Rhodamine Red, Rhodamine 110, BODIPY dyes, such as BODIPY TMR, Oregon Green, Coumarines such as Umbelliferone, Benzimides, such as Hoechst 33258; Phenanthridines, such as Texas Red, Yakima Yellow, Alexa Fluor, PET, Ethidiumbromide, Acridinium dyes, Carbazol dyes, Phenoxazine dyes, Porphyrine dyes, Polymethin dyes, and the like.

In the context of the present invention, chemiluminescence based assays comprise the use of dyes, based on the physical principles described for chemiluminescent materials in Kirk-Othmer, Encyclopedia of chemical technology, 4th ed., executive editor, J. I. Kroschwitz; editor, M. Howe-Grant, John Wiley & Sons, 1993, vol. 15, p. 518-562, incorporated herein by reference, including citations on pages 551-562. Preferred chemiluminescent dyes are acridiniumesters. Free histone proteins may for example be detected using fully automated sandwich immunoassay systems on the B.R.A.H.M.S KRYPTOR compact PLUS instrument (Thermo Scientific B.R.A.H.M.S GmbH, Hennigsdorf/Berlin, Germany). This random access analyzer employs the sensitive Time Resolved Amplified Cryptate Emmission (TRACE) technology, based on a non-radioactive-transfer between two fluorophores.

The invention further relates to a method wherein one of the antibodies (e.g. the first antibody) is labeled and the other antibody (e.g. the second antibody) is bound to a solid phase or can be bound selectively to a solid phase. However, as mentioned above, it is preferred in the context of methods of the invention that the first and the second antibody are present dispersed in a liquid reaction mixture, and wherein a first labelling component which is part of a labelling system based on fluorescence or chemiluminescence extinction or amplification is bound to the first antibody, and a second labelling component of said labelling system is bound to the second antibody so that, after binding of both antibodies to a histone protein (or fragment(s) thereof), a measurable signal which permits detection of the resulting sandwich complexes in the measuring solution is generated.

As mentioned herein, an "assay" or "diagnostic assay" can be of any type applied in the field of diagnostics. Such an assay may be based on the binding of an analyte to be detected to one or more capture probes with a certain affinity. Concerning the interaction between antibodies and target molecules or molecules of interest, the affinity constant is preferably greater than $10^8$ M$^{-1}$.

The invention further relates to an antibody or an antigen-binding fragment or derivative thereof as mentioned above which is specific for an epitope of a free histone protein or fragment thereof as already detailed above.

The appended examples document exemplary antibodies that are successfully employed to detect free histones according to the invention. The present invention thus relates to an antibody, an antigen-binding fragment or derivative thereof that is specific for an epitope of a free histone H4, H2A, H2B, and/or H3. Furthermore, the present invention relates to an antibody, an antigen-binding fragment or derivative thereof being specific for an epitope of a free histone H4 comprised in the sequence spanning amino acid residues 22 to 102 of said histone H4 according to SEQ ID NO:1.

Furthermore, the present invention relates to an antibody, an antigen-binding fragment or derivative thereof being specific for an epitope of a free histone H4 comprised in the sequence spanning amino acid residues 46 to 102 of histone H4 according to SEQ ID NO:1.

More preferably, the present invention relates to an antibody, an antigen-binding fragment or derivative thereof being specific for an epitope of free histone H4 comprised in the sequence selected from the group consisting of an amino acid sequence spanning residues 22 to 30 of SEQ ID NO:1, residues 67 to 78 of SEQ ID NO:1, residues 92 to 102 of SEQ ID NO:1, residues 22 to 34 of SEQ ID NO: 1, residues 46 to 102 of SEQ ID NO:1, residues 46 to 55 of SEQ ID NO:1, residues 60 to 67 of SEQ ID NO:1, residues 80 to 91 of SEQ ID NO:1, residues 24 to 35 of SEQ ID NO:1, and residues 68 to 77 of SEQ ID NO:1.

Furthermore, the present invention relates to an antibody, an antigen-binding fragment or derivative thereof being specific for an epitope of a free histone H2A comprised in the sequence spanning amino acid residues 20 to 118 of histone H2A according to SEQ ID NO:23.

More preferably, the present invention relates to an antibody, an antigen-binding fragment or derivative thereof being specific for an epitope of a free histone H2A comprised in the sequence selected from the group consisting of an amino acid sequence spanning residues 21 to 53 of SEQ ID NO:23, residues 21 to 29 of SEQ ID NO:23, residues 30 to 53 of SEQ ID NO:23, residues 120 to 129 of SEQ ID NO: 23, residues 21 to 29 of SEQ ID NO: 23, residues 82 to 88 of SEQ ID NO: 23, residues 89 to 95 of SEQ ID NO: 23, and residues 100 to 118 of SEQ ID NO: 23.

Furthermore, the present invention relates to an antibody, an antigen-binding fragment or derivative thereof being specific for an epitope of a free histone H3 comprised in the sequence spanning amino acid residues 27 to 62 of histone H3 according to SEQ ID NO:36.

More preferably, the present invention relates to an antibody, an antigen-binding fragment or derivative thereof being specific for an epitope of free histone H3 comprised in the sequence spanning residues 27 to 37 of SEQ ID NO: 36 and/or residues 52 to 62 of SEQ ID NO: 36.

Furthermore, the present invention relates to an antibody, an antigen-binding fragment or derivative thereof being specific for an epitope of free histone H2B comprised in the sequence spanning amino acid residues 41 to 69 of histone H2B according to SEQ ID NO:31.

Particularly preferred in the context of the invention is an antibody or an antigen-binding fragment or derivative thereof which is specific for an epitope of histone H2A in the sequence spanning amino acid residues 20 to 55 or 70 to 118 of free histone H2A according to SEQ ID NO:23 or an antibody or an antigen-binding fragment or derivative thereof which is specific for an epitope of histone H4 present in the sequence spanning amino acid residues 46 to 102 of SEQ ID NO: 1. In other words, in preferred aspects of the invention, the antibody or antigen-binding fragment or derivative thereof is specific for an epitope given in SEQ ID NO:2.

The invention further relates to a host cell which expresses the antibody or antigen-binding fragment or derivative thereof of the invention.

In the context of the invention, the term "host cells" refers to any cell expressing the antibody or antigen-binding fragment or derivative thereof of the invention. Accordingly, prokaryotic as well as eukaryotic cells are in the scope of the invention.

The invention also relates to a kit comprising an antibody or an antigen-binding fragment or derivative thereof of the invention. The aforementioned antibodies of the invention can be used in the kit of the invention.

Also encompassed by the invention is the use of the antibody or antigen-binding fragment or derivative thereof of the invention or the use of the kit of the invention in a method for the diagnosis, prognosis, risk assessment and/or therapy control of a disease or a medical condition selected from diseases or medical conditions that involve the systemic inflammatory response (SIRS) of an individual related to infective and non-infective etiologies such as sepsis, severe sepsis and septic shock caused by microbial stimuli i.e. bacteria, viruses, fungi and/or parasites, traumatic injury and/or hemorrhage, ischemia reperfusion injury, burn injuries, acute pancreatitis as well as interventional procedures such as e.g. cardio-pulmonary bypass, chemotherapy and radiotherapy where an individual is at risk of developing, endothelial tissue damage, thromboembolism and acute disseminated intravascular coagulation, (DIC) contributing to single or multiple organ dysfunction and failure (in particular acute kidney injury, acute lung injury and liver injury) during the course of the disease.

Mass Spectrometry Based-Methods

According to the present invention, the free histone molecule may be detected using mass spectrometry (MS) methods. Hence, the present invention also provides a method for the diagnosis, prognosis, risk assessment, risk stratification and/or therapy control of the above-defined diseases or medical conditions, comprising detecting at least one free histone protein or peptide fragment thereof in a sample by mass spectrometry (MS). Consequently, the invention relates to the use of MS for the diagnosis, prognosis, risk assessment, screening and therapy monitoring of the above-mentioned disorders or medical conditions in a patient.

The invention also relates to a method for measuring the amount of free histone proteins in a biological sample, said method comprising detecting the presence or amount of one or more modified or unmodified histone fragment peptides in said biological sample or a protein digest (e.g. tryptic digest) from said sample and optionally separate the sample with chromatographic methods, and subjecting the prepared and optionally separated sample to MS analysis. For example, selected reaction monitoring (SRM), multiple reaction monitoring (MRM) or parallel reaction monitoring (PRM) mass spectrometry may be used in the MS analysis, particularly to determine the amounts of at least one histone peptide.

In one aspect of the MS analysis method of the invention it is not required to pre-separate the proteins in the sample prior to proteolytic digestion. A reliable detection of free histones and peptides thereof can be achieved without separation methods that comprise delipidation, chromatography, centrifugation, or affinity matrices that deplete abundant proteins.

Herein, the term "mass spectrometry" or "MS" refers to an analytical technique to identify compounds by their mass. MS refers to methods of filtering, detecting, and measuring ions based on their mass-to-charge ratio, or "m/z." "MS" technology is characterized by (1) ionization of compounds to generate charged compounds and (2) detection of the mass-to-charge ratios of the charged compounds. The compounds are generally ionized by an ionizer and detected by an ion detector. Ionizer and ion detector are incorporated in a mass spectrometer. In general, one or more molecules of interest are ionized, and the ions are subsequently introduced into a mass spectrographic instrument where the ions are separated according to their m/z's. Such separation may be performed on the basis of m/z-dependent behavior of ions in electric fields (or a combination of electric and magnetic fields), or time-of-flight variations in a field-free region of ions having m/z-dependent kinetic energies. See, e.g., U.S. Pat. No. 6,204,500, entitled "Mass Spectrometry From Surfaces"; U.S. Pat. No. 6,107,623, entitled "Methods and Apparatus for Tandem Mass Spectrometry"; U.S. Pat. No. 6,268,144, entitled "DNA Diagnostics Based On Mass Spectrometry"; U.S. Pat. No. 6,124,137, entitled "Surface-Enhanced Photolabile Attachment And Release For Desorption And Detection Of Analytes"; Wright et al., Prostate Cancer and Prostatic Diseases 2:264-76 (1999); and Merchant and Weinberger, Electrophoresis 21: 1164-67 (2000).

In general, MS detection and analysis can be performed in different ways, depending on the aim of the analysis. Top-down proteomics relates to an intact analysis, which maintains the protein integrity for the detection of degradation products, sequence variants and combinations of post-translational modifications. Bottom-up peptide analysis involves the reduction, alkylation, and digestion of purified protein samples to access and analyze peptide fragments.

In order to enhance the mass resolving and mass determining capabilities of mass spectrometry, the samples can be processed prior to MS analysis. Accordingly, the invention relates to MS detection methods that can be combined with immuno-enrichment technologies, methods related to sample preparation and/or chromatographic methods, preferably with liquid chromatography (LC), more preferably with high performance liquid chromatography (HPLC) or ultra high performance liquid chromatography (UHPLC). Sample preparation methods comprise techniques for lysis, fractionation, digestion of the sample into peptides, depletion, enrichment, dialysis, desalting, alkylation and/or peptide reduction. However, these steps are optional. In one aspect of the invention, no proteolytic (e.g. tryptic) digestion is necessary to measure a fragment, e.g SEQ NO: 2. The sample can be subjected to immuno-enrichment prior to MS analysis. Mass spectrometric immunoassay technologies such as the Thermo Fisher MSIA™ technology may be applied prior to digestion, or SISCAPA® technology after digestion.

Single-, or multidimensional HPLC may be used for separating proteins or peptides. The protein or peptide mixture may be passed through a succession of chromatographic stationary phases or dimensions which gives a higher resolving power. HPLC is adaptable for many experimental approaches and various stationary and mobile phases can be selected for their suitability in resolving specific protein or peptide classes of interest and for compatibility with each other and with downstream mass spectrometric methods of detection and identification. HPLC may be used to separate clinical samples that have been digested or not by a proteolytic enzyme where the corresponding enzyme products, the peptide mixtures, are generated. The corresponding peptide mixture may be passed through a succession of chromatographic stationary phases or dimensions which gives a high resolving power. The separation of peptides and proteins is based on the peptide sequence, the functional groups of the peptide sequence, as well as the physical properties.

Hence, the mass spectrometrical detection can be combined with the application of liquid chromatography (LC), which is performed before the mass spectrometrical detection. More preferred, a high-performance liquid chromatography (HPLC) is performed prior to the mass detection.

In preferred aspects of the invention, the MS-based methods are not dependent on preparatory protein purification prior to proteolytic digestion. Further, the removal of biochemical compounds such as lipids, proteins or DNA may not be required prior to proteolytic digestion. In preferred aspects, purification steps separating the proteins in accordance to their physical properties, i.e., chromatography or centrifugation may not be required prior to proteolytic digestion. Further, the depletion of abundant or medium abundant proteins may not be required prior to proteolytic digestion. Abundant proteins can be removed by matrices such as Ig-Y12 columns. In the context of this invention such pre-separation steps are referred to as pre-separation prior to proteolytic digestion. Accordingly, the free histone proteins in the biological sample such as serum or plasma may be detected without any pre-treatment or pre-separation prior to proteolytic digestion.

In certain aspects, the biological sample can be subjected to MS analysis without prior separation procedures, whereby immuno-enrichment techniques and pre-treatment procedures can be conducted. In such an embodiment, the sample is preferably analyzed by direct infusion using static electrospray principles, flow injection analysis or flow injection with sample enrichment.

As used herein, the term "ionizing" or the "ionization" of sample molecules refers to different techniques that create an analyte ion having a net electrical charge equal to one or more electron units. Said technique may be chemical ionization (CI), electron ionization (EI), fast atom bombardment (FAB), matrix-assisted laser desorption ionization (MALDI), electrospray ionization (ESI), surface-enhanced laser desorption ionization (SELDI), atmospheric pressure chemical ionization (APCI), atmospheric pressure photoionization (APPI), inductively coupled plasma (ICP), field desorption (FD), thermospray, desorption/ionization on silicon (DIOS), secondary ion mass spectrometry (SIMS), spark ionization, thermal ionization or ion attachment ionization.

The selective detection of analyte ions may be conducted with tandem mass spectrometry (MS/MS). Tandem mass spectrometry is characterized by mass selection step (as used herein, the term "mass selection" denotes isolation of ions having a specified m/z or narrow range of m/z's), followed by fragmentation of the selected ions and mass analysis of the resultant product (fragment) ions.

The precursor analyte ion can be fragmented by using different techniques, which can be selected from collision-induced dissociation (CID), multi-stage activation (MSA), pulsed-q dissociation (PQD), electron-transfer dissociation (ETD), heated capillary dissociation (HTD), electron-capture dissociation (ECD) or infrared multi-photon dissociation (IRMPD), higher-energy C-trap dissociation (HCD).

As used herein, tandem mass spectrometry is preferably performed by using a triple quadrupole tandem mass spectrometer. A tandem mass spectrometer is characterized in that the first and third quadrupoles are mass filters, i.e., capable of selectively transmitting ions of a desired m/z or narrow range of m/z's. The second quadrupole is employed for the collision-induced dissociation. Precursor analyte ions are selected in the first quadrupole and dissociated in the second quadrupole through collision with a neutral gas. The third quadrupole filters the ionized fragments, which are further detected by a detection system, optionally including an electron multiplier (Hoffmann E., Journal of Mass Spectrometry, Vol. 31, 1996, 129-137).

As outlined herein a triple quadrupole tandem mass spectrometer can be used for performing selected reaction monitoring (SRM), also called multiple reaction monitoring (MRM), and quantitative selected reaction monitoring (qSRM).

Alternatively, assays may utilize parallel reaction monitoring (PRM) for detection and quantification of the target analytes. In contrast to MRM, which, as described below, serially detects and quantifies different product ions by switching between or among characteristic transitions, PRM simultaneously detects and quantifies two or more product ions resulting from fragmentation of a common precursor ion. Generally, PRM entails the accumulation and subsequent mass analysis of different product ion species. In one non-limiting example, PRM may be performed on the Q Exactive mass spectrometer available from Thermo Fisher Scientific (Bremen, Germany). In the Q Exactive mass spectrometer, precursor ions of a specified m/z are selectively transmitted by a quadrupole mass filter to a collision cell, wherein they collide at relatively high energies with molecules or atoms of a neutral gas and consequently undergo collision-induced dissociation to form product ions. The collected product ions, which include different ion species having various m/z's, are then delivered to an orbital electrostatic trap (Orbitrap) mass analyzer, which mass analyzes the product ions to generate a mass spectrum representing the individual abundances (intensities) of each of a plurality of product ion species.

The detection methods may comprise assays in formats such as Selected/Multiple reaction monitoring (SRM/MRM).

It is preferred in this context that a triple quadrupole tandem mass spectrometer is used for performing SRM/MRM. SRM or quantitative selected reaction monitoring (qSRM) is a technique for precise analysis and quantification of compounds (proteins) in complex biological samples yielding a high level of selectivity and sensitivity. As used herein, "qSRM" refers to a selected reaction monitoring as described below, where selected peptides are quantified by using isotopically labeled reference peptides or full-length proteins.

As used herein, the term "SRM" defines a technique, where a special precursor analyte (peptide as surrogates for target proteins, here the free histone protein(s) to be detected) is selected and isolated within the mass spectrometer. The ionized precursor analyte is fragmented and the ionized fragments are monitored for detection and quantification based on their mass-to-charge ratios. The specific pairs of m/z values associated to the precursor and fragment ions are referred to as "transitions".

Said "transitions" refer to a specific pair of precursor/fragment ion m/z values to which the first and third quadrupoles are tuned. Said "transition" is essential for the identification and quantification of a specific peptide, which is a surrogate for a protein of interest in a complex protein digest. In average, 2-4 transitions of the surrogate and the synthetic isotopically-labeled reference peptide are measured in a qSRM assay. For the application of SRM/qSRM measurements, it is suggested to have at least two transitions for each peptide to ensure specificity and no misidentification of targeted substances.

Generally, the establishment of a SRM/MRM assay starts with the selection of a peptide or peptides after the protein of interest is digested. Suitable peptides (precursor analyte) show a significant high mass spectrometry signal response. Secondly, peptide fragments are selected, which are specific for the precursor analyte. For each precursor analyte-fragment an optimization of specific MS parameters including collision energy, ion optic settings and dwell time may be carried out. The following validation of the transitions confirms the detectability in biological samples (e.g. plasma/serum) and assesses background. By adding isotopically labeled standard peptides, the precursor analyte can be quantified. For the selection of peptides and fragments, prediction tools (e.g. a software programme with an algorithmic prediction, databases) can be used to help to choose optimal transitions.

As outlined above, the invention refers in one aspect to the detection and/or quantification of free histone proteins in biological samples, whereby a method is used comprising the application of liquid chromatography and a SRM and/or qSRM assay, that specifically detects histone peptides as being surrogate peptides for the free histone protein.

In certain implementations, it may be beneficial to utilize a high resolution/accurate mass (HRAM) mass analyzer for detection and measurement of precursor and/or product ions formed from the free histone proteins or peptides derived therefrom. HRAM mass analyzers are those mass analyzers that are capable of acquiring mass spectra at resolving powers typically exceeding 15K and with mass accuracy typically less than 5 parts-per-million (ppm). Examples of HRAM mass analyzers include the Fourier Transform/Ion Cyclotron Resonance (FT-ICR) analyzer, the Orbitrap orbital electrostatic trap analyzer, and certain multi-reflection or long-path time-of-flight (TOF) analyzers. Mass spectrometer instruments that incorporate an HRAM mass spectrometer include the Exactive and Q Exactive product lines available from Thermo Fisher Scientific (Bremen, Germany). Generally, HRAM mass analyzers enable target analytes to be distinguished in the mass spectrum from interfering ion species having closely similar m/z's, thereby facilitating confident identification and quantification of the target analyte (e.g., an ion formed from a free histone or its surrogate peptide). In this manner, target analytes may be detected and measured with high selectivity in a complex biological matrix, such as blood plasma. Use of an HRAM mass analyzer may permit the omission or simplification of sample preparation and separation techniques intended to isolate the target analyte(s) from interfering components in the sample whose presence could confound measurement of the target analyte(s) by mass spectrometry. In certain applications, use of an HRAM analyzer may allow the confident detection and quantification of target analytes using precursor ion abundances (for example, based on intensities appearing in a full MS spectrum), obviating the need for a fragmentation step.

Relative quantification "rSRM" may be achieved by:

1. Determining increased or decreased presence of the free histones proteins by comparing the SRM signature peak area from a given histone peptide detected in biological sample to the same SRM signature peak area of the same histone fragment peptide in at least a second, third, fourth or more biological samples.

2. Determining increased or decreased presence of free histones proteins by comparing the SRM signature peak area from a given histones peptide detected in a biological sample to SRM signature peak areas developed from fragment peptides from other proteins, in other samples derived from different and separate biological sources, where the SRM signature peak area comparison between the two samples for a peptide fragment are normalized for e.g to amount of protein analyzed in each sample.

3. Determining increased or decreased presence of the histones protein by comparing the SRM signature peak area for a given histones peptide to the SRM signature peak areas from other fragment peptides derived from different proteins within the same biological sample in order to normalize changing levels of histones protein to levels of other proteins that do not change their levels of expression under various cellular conditions.

4. These assays can be applied to both unmodified fragment peptides and to modified fragment peptides of the histone proteins, where the modifications include, but are not limited to phosphorylation and/or glycosylation, acetylation, methylation (mono, di, tri), citrullination, ubiquitinylation and where the relative levels of modified peptides are determined in the same manner as determining relative amounts of unmodified peptides.

Absolute quantification of a given peptide may be achieved by:

1. Comparing the SRM/MRM signature peak area for a given fragment peptide from the histone proteins in an individual biological sample to the SRM/MRM signature peak area of an internal fragment peptide standard spiked into the protein lysate from the biological sample.

The internal standard may be a labeled synthetic version of the fragment peptide from the histones protein that is being interrogated or the labeled recombinant protein. This standard is spiked into a sample in known amounts before (mandatory for the recombinant protein) or after digestion, and the SRM/MRM signature peak area can be determined for both the internal fragment peptide standard and the native fragment peptide in the biological sample separately, followed by comparison of both peak areas. This can be applied to unmodified fragment peptides and modified fragment peptides, where the modifications include but are not limited to phosphorylation and/or glycosylation, acetylation, methylation (mono, di, tri), citrullination, ubiquitinylation, and where the absolute levels of modified peptides can be determined in the same manner as determining absolute levels of unmodified peptides.

2. Peptides can also be quantified using external calibration curves. The normal curve approach uses a constant amount of a heavy peptide as an internal standard and a varying amount of light synthetic peptide spiked into the sample. A representative matrix similar to that of the test samples needs to be used to construct standard curves to account for a matrix effect. Besides, reverse curve method circumvents the issue of endogenous analyte in the matrix, where a constant amount of light peptide is spiked on top of the endogenous analyte to create an internal standard and varying amounts of heavy peptide are spiked to create a set of concentration standards. Test samples to be compared with either the normal or reverse curves are spiked with the same amount of standard peptide as the internal standard spiked into the matrix used to create the calibration curve.

As explained above, the amount of free histone proteins in the biological sample may be measured by detecting the amount of one or more modified or unmodified histone fragment peptides in a protein digest from said biological sample and optionally separating the sample with chromatographic methods, and subjecting the prepared and optionally separated sample to selected reaction monitoring (SRM) tandem mass spectrometry to determine the amounts of at least one histone peptide.

The invention also relates to a method for measuring the amount of free histone proteins in a sample, said method comprising detecting the amount of one or more modified or unmodified histone fragment peptides in a protein digest from said biological sample and optionally separate the sample with chromatographic methods, and subjecting the prepared and optionally separated sample to selected reaction monitoring (SRM) tandem mass spectrometry to determine the amounts of at least one histone peptide. The quantification of the histone fragment peptides can be a relative quantification by rSRM or an absolute quantification.

The invention also provides a method for measuring the amount of free histone proteins in a sample, said method comprising detecting the amount of one or more histone fragment peptides in a protein digest from said biological sample without pre-separation of said sample prior to proteolytic digestion, and subjecting separated peptides to selected reaction monitoring (SRM) tandem mass spectrometry to determine the amounts of at least one histone peptide.

The invention also relates to a method for measuring the amount of free histone proteins in a sample, said method comprising detecting the amount of one or more modified or unmodified histone fragment peptides in a protein digest from said biological sample without pre-separation of said sample prior to proteolytic digestion, and subjecting separated peptides to selected reaction monitoring (SRM) tandem mass spectrometry to determine the amounts of at least one histone peptide.

Further, the invention relates to a method for measuring the amount of free histone proteins in a sample, said method comprising detecting the amount of one or more unmodified histone fragment peptides in a protein digest from said biological sample without pre-separation of said sample prior to proteolytic digestion, and subjecting separated peptides to selected reaction monitoring (SRM) tandem mass spectrometry to determine the amounts of at least one histone peptide.

Further, the invention relates to a method for measuring the amount of free histone proteins in a sample, said method comprising detecting the amount of one or more unmodified histone fragment peptides without proteolytical digestion from said biological sample, but with applying pre-treatment procedures or immune-enrichment procedures before pre-separation of said sample and subjecting separated peptides to selected reaction monitoring (SRM) tandem mass spectrometry to determine the amounts of at least one free histone peptide.

Thus, the invention also relates to a method for measuring the amount of free histone proteins in a sample which has not been subjected to proteolytic (e.g. tryptic) digestion, said method comprising detecting the amount of one or more histone fragment peptides by selected reaction monitoring (SRM) tandem mass spectrometry to determine the amounts of at least one free histone peptide, wherein the sample has been subjected to pre-treatment procedures or immune-enrichment procedures prior to detection.

The following illustrative and exemplary assay can also be used in the context of the present invention, however, other assays can equally be applied. The sample is proteolytically digested, preferably by adding proteases (e.g. trypsin), which results in a sample containing histone peptides (surrogate peptides) specific for the histone protein. For exact quantification of the surrogate peptide, an internal standard is added in defined amounts to the sample. Therefore, isotopically-labeled synthetic peptide is added and represents the counterpart of surrogate peptide. The internal standard may also be added prior to the proteolytic digestion. The digested sample containing the surrogate peptides and the corresponding internal standard is now chromatographically separated applying a suitable LC/HPLC protocol (HPLC column, gradient, elution time). As used herein, the chromatographic separation is performed on-line, whereby the column eluate is directly transferred to the first ionization unit of the mass spectrometer. Alternatively, different eluates may be collected first and analyzed afterwards. Apart from liquid chromatography, different techniques for sample separation, such as described in a previous paragraph, may be applied. After the separation step, the mass of the selected surrogate peptide and corresponding fragments will be determined by using a mass spectrometer, preferably by using a tandem mass spectrometer. The sample, containing histone peptides, is ionized in the mass spectrometer and the resultant ions are delivered to a first mass filter. As previously described, only ionized peptides with the mass-to-charge ratio (m/z) of interest are selectively introduced into the collision unit, where the precursor peptides undergo fragmentation because of collisions with the collision gas. The selected peptide fragment ions are further transmitted to the second mass filter. After detection, a signal is generated, which represents the quantity of the transmitted histone peptide fragment ions.

The antibodies or antigen-binding fragments or derivatives thereof described in the context of the immunoassay methods of the invention can also be used to immunoprecipitate/immunopurify free histones prior to MS analysis, whereby a protease digestion can be applied or not.

Accordingly, the invention relates to a method for measuring the presence or amount of free histone protein(s) in the biological sample, wherein the method comprises immunopurifying free histone proteins using an antibody or an antigen-binding fragment or a derivative thereof, which is specific for an epitope comprised in the histone protein, separating the sample with chromatographic methods, detecting the amount of one or more modified or unmodified histone fragment peptides from said biological sample and subjecting the prepared sample to MS analysis.

As outlined herein above, in the MS-based methods of the present invention the sample may be subjected to a protease digestion, preferably tryptic digestion prior to MS analysis. However, in other aspects of the invention the sample is not subjected to a protease digestion, preferably tryptic digestion prior to MS analysis.

In accordance with the above explanations, the MS-based methods of the invention may optionally comprise one or more of the following steps:
(i) subjecting the sample to a pre-treatment such as addition of chemical or biochemical substances
(ii) subjecting the sample to a reduction and/or alkylation reaction;
(iii) separating the sample with a chromatographic method before the MS analysis and after tryptic digest;
(iv) enriching the sample using an immunoaffinity device (such as the Thermo Scientific MSIA™ technology) or depleting unwanted components using depletion columns.
(v) adding at least one internal reference standard, wherein the reference standard is an isotopically-labeled version of the peptide, or the protein to be detected.

In the MS-based methods of the invention, the free histone protein may be histone H2A and at least a peptide fragment thereof selected from the group consisting of SEQ ID NOs:24, 28, 29 and 30, preferably peptide fragments selected from SEQ ID NOs:24 and 28 are detected and optionally quantified.

In the MS-based methods of the invention the free histone protein may also be histone H4 and at least a peptide fragment thereof selected from the group consisting of SEQ ID NOs:2, 3, 4, 5, 6 and 7, preferably peptide fragments selected from SEQ ID NOs:3 and 4 are detected and optionally quantified.

Preferred peptide fragments and transitions in the context of the present invention are listed in Tables 4 and 5.

All references cited herein including scientific literature and patent documents are herewith incorporated by reference.

Sequences (amino acid sequence of human histone H4, uniprot ID P62805.2, initial methionine not included)

SEQ ID NO: 1

```
  1 SGRGKGGKGL GKGGAKRHRK VLRDNIQGIT KPAIRRLARR GGVKRISGLI
 51 YEETRGVLKV FLENVIRDAV TYTEHAKRKT VTAMDVVYAL KRQGRTLYGF
101 GG
```

(amino acid sequence of residues 46-102 of SEQ ID NO: 1)

SEQ ID NO: 2

```
 1 ISGLIYEETR GVLKVFLENV IRDAVTYTEH AKRKTVTAMD VVYALKRQGR
51 TLYGFGG
```

(amino acid sequence of residues 46-55 of SEQ ID NO: 1)

SEQ ID NO: 3

```
1 ISGLIYEETR
```

(amino acid sequence of residues 60-67 of SEQ ID NO: 1)

SEQ ID NO: 4

```
1 VFLENVIR
```

(amino acid sequence of residues 80-91 with acetylated K91 of SEQ ID NO: 1)

SEQ ID NO: 5

```
1 TVTAMDVVYAL K
```

(amino acid sequence of residues 24-35 of SEQ ID NO: 1)

SEQ ID NO: 6

```
1 DNIQGITKPA IR
```

(amino acid sequence of residues 68-77 of SEQ ID NO: 1)

SEQ ID NO: 7

```
1 DAVTYTEHAK
```

(amino acid sequence of H4-GR-17, position 2-17 of SEQ ID NO: 1)

SEQ ID NO: 8

```
1 GRGKGGKGLG KGGAKR
```

(amino acid sequence of H4-GH-18, position 2-18 of SEQ ID NO: 1)

SEQ ID NO: 9

```
1 GRGKGGKGLG KGGAKRH
```

(amino acid sequence of H4-LI-9, position 22-30 of SEQ ID NO: 1)

SEQ ID NO: 10

```
1 LRDNIQGIT
```

(amino acid sequence of H4-LR-15, position 22-35 of SEQ ID NO: 1)

SEQ ID NO: 11

```
1 LRDNIQGITK PAIR
```

(amino acid sequence of H4-LL-17, position 22-37 of SEQ ID NO: 1)

SEQ ID NO: 12

```
1 LRDNIQGITK PAIRRL
```

(amino acid sequence of H4-PR-15, position 32-45 of SEQ ID NO: 1)

SEQ ID NO: 13

```
1 PAIRRLARRG GVKR
```

(amino acid sequence of H4-PS-17, position 32-47 of SEQ ID NO: 1)

SEQ ID NO: 14

```
1 PAIRRLARRG GVKRIS
```

(amino acid sequence of H4-EE-13, position 52-63 of SEQ ID NO: 1)

SEQ ID NO: 15

```
1 EETRGVLKVF LE
```

(amino acid sequence of H4-EN-14, position 52-64 of SEQ ID NO: 1)

SEQ ID NO: 16

```
1 EETRGVLKVF LEN
```

(amino acid sequence of H4-RR-13, position 67-78 of SEQ ID NO: 1)

SEQ ID NO: 17

```
1 RDAVTYTEHA KR
```

(amino acid sequence of H4-RK-14, position 67-79 of SEQ ID NO: 1)

SEQ ID NO: 18

```
1 RDAVTYTEHA KRK
```

-continued (amino acid sequence of H4-TK-13, position 80-91 of SEQ ID NO: 1)
SEQ ID NO: 19
```
  1 TVTAMDVVYA LK
```

(amino acid sequence of H4-TR-14, position 80-92 of SEQ ID NO: 1)
SEQ ID NO: 20
```
  1 TVTAMDVVYA LKR
```

(amino acid sequence of H4-RG-9, position 92-99 of SEQ ID NO: 1)
SEQ ID NO: 21
```
  2 RQGRTLYG
```

(amino acid sequence of H4-RG-12, position 92-102 of SEQ ID NO: 1)
SEQ ID NO: 22
```
  3 RQGRTLYGFG G
```

(amino acid sequence of human histone H2A type 1, uniprot ID Q96QV6, initial methionine not included)
SEQ ID NO: 23
```
  1 SGRGKQGGKA RAKSKSRSSR AGLQFPVGRI HRLLRKGNYA ERIGAGAPVY

51 LAAVLEYLTA EILELAGNAS RDNKKTRIIP RHLQLAIRND EELNKLLGGV

101 TIAQGGVLPN IQAVLLPKKT ESHHHKAQSK
```

(amino acid sequence of HA-AR-10, position 21-29 of SEQ ID NO: 23)
SEQ ID NO: 24
```
  1 AGLQFPVGR
```

(amino acid sequence of HA-AH-12, position 21-31 of SEQ ID NO: 23)
SEQ ID NO: 25
```
  1 AGLQFPVGRI H
```

(amino acid sequence of HA-IL-23, position 30-51 of SEQ ID NO: 23)
SEQ ID NO: 26
```
  1 IHRLLRKGNY AERIGAGAPV YL
```

(amino acid sequence of HA-IA-25, position 30-53 of SEQ ID NO: 23)
SEQ ID NO: 27
```
  1 IHRLLRKGNY AERIGAGAPV YLAA
```

(amino acid sequence of residues 82-88 of SEQ ID NO: 23)
SEQ ID NO: 28
```
  1 HLQLAIR
```

(amino acid sequence of residues 89-95 of SEQ ID NO: 23)
SEQ ID NO: 29
```
  1 NDEELNK
```

(amino acid sequence of residues 100-118 of SEQ ID NO: 23)
SEQ ID NO: 30
```
  1 VTIAQGGVLP NIQAVLLPK
```

(amino acid sequence of human histone H2B, uniprot ID P62807)
SEQ ID NO: 31
```
  1 MPEPAKSAPA PKKGSKKAVT KAQKKDGKKR KRSRKESYSV YVYKVLKQVH

51 PDTGISSKAM GIMNSFVNDI FERIAGEASR LAHYNKRSTI TSREIQTAVR

101 LLLPGELAKH AVSEGTKAVT KYTSSK
```

(amino acid sequence of residues 94-100 of SEQ ID NO: 31)
SEQ ID NO: 32
```
  1 EIQTAVR
```

(amino acid sequence of residues 101-109 of SEQ ID NO: 31)
SEQ ID NO: 33
```
  1 LLLPGELAK
```

(amino acid sequence of human histone H2B, uniprot ID Q6DN03.3, initial methionine not included)
SEQ ID NO: 34
```
  1 MPEPAKFAPA PKKGSKKAVT KAQKKDGKKR KRSRKESYSI YVYKVLKRVH

51 PDTGIWCKAM GIMNSFLNDI FERIAGEASR LAHYNKRSTI TSRRSRRPCA

101 CCCPASWPST PCPRAPRRSP STPAPSESLP GPGARSLPPS LPPRVAGCFV

151 SKGSFQGHLT TSVKESFLCC QSQLMFLASR LVNFRRAHNT KHR
```

-continued (amino acid sequence of residues 181-193 of SEQ ID NO: 34)
SEQ ID NO: 35

```
  1 LVNFRRAHNTKHR
```

(amino acid sequence of human histone H3.1, uniprot ID P68431.2, initial methionine not included)
SEQ ID NO: 36

```
  1 ARTKQTARKS TGGKAPRKQL ATKAARKSAP ATGGVKKPHR YRPGTVALRE

51 IRRYQKSTEL LIRKLPFQRL VREIAQDFKT DLRFQSSAVM ALQEACEAYL

101 VGLFEDTNLC AIHAKRVTIM PKDIQLARRI RGERA
```

(amino acid sequence of residues 57-63 of SEQ ID NO: 36)
SEQ ID NO: 37

```
  1 STELLIR
```

(amino acid sequence of residues 117-122 of SEQ ID NO: 36)
SEQ ID NO: 38

```
  1 VTIMPK
```

(amino acid sequence of residues 41-49 of SEQ ID NO: 36)
SEQ ID NO: 39

```
  1 YRPGTVALR
```

(amino acid sequence of human histone H2A type 3, uniprot ID Q7L7L0.3, initial methionine not included), Sigma recombinant H2A SRP0406
SEQ ID NO: 40

```
  1 SGRGKQGGKA RAKAKSRSSR AGLQFPVGRV HRLLRKGNYS ERVGAGAPVY

51 LAAVLEYLTA EILELAGNAA RDNKKTRIIP RHLQLAIRND EELNKLLGRV

101 TIAQGGVLPN IQAVLLPKKT ESHHKAKGK
```

(amino acid sequence of human histone H1, uniprot ID P07305, initial methionine not included)
SEQ ID NO: 41

```
  1 TENSTSAPAA KPKRAKASKK STDHPKYSDM IVAAIQAEKN RAGSSRQSIQ

51 KYIKSHYKVG ENADSQIKLS IKRLVTTGVL KQTKGVGASG SFRLAKSDEP

101 KKSVAFKKTK KEIKKVATPK KASKPKKAAS KAPTKKPKAT PVKKAKKKLA

151 ATPKKAKKPK TVKAKPVKAS KPKKAKPVKP KAKSSAKRAG KKK
```

EXAMPLES

The following examples and figures are used for a more detailed explanation of the invention, but do not limit the invention to said examples and figures.

Example 1: Generation of Antibodies

A. Peptides

Peptides related to histone H4 amino acid sequence were chemically synthesized and purified (>90%) by Thermo Fisher Scientific GmbH, Ulm, Germany, New England Peptide Inc, Gardner, Mass., USA, or JPT Peptide Technologies GmbH. Immunization peptides were either conjugated to bovine serum albumin using sulfo-MBS (m-maleimidobenzoyl-N-hydroxysuccinimid ester (BSA, Sigma Aldrich) or to keyhole limpet hemocyanin (KLH, Thermo Fisher Scientific) via an additional N-terminal cysteine. Peptides used for affinity purification of the antibodies contained one or two additional C-terminal amino acids as compared to the peptides used for immunization and an additional N-terminal cysteine for immobilization to the SulfoLink coupling resin.

B. Development of Polyclonal Antibodies

Sheep polyclonal antibodies directed against H4-LI-9 (amino acids 22-30 of histone H4, SEQ ID NO:10), H4-EE-13 (amino adds 52-63 of histone H4, SEQ ID NO:15), H4-RR-13 (amino acids 67-78 of histone H4, SEQ ID NO:17), and H4-RG-9 (amino acids 92-99 of histone H4, SEQ ID NO:21) were generated according to standard procedures (see EP 1488209 A1, EP 1738178 A1). Briefly, peptides were coupled to the carrier protein KLH using MBS via an extra N-terminal cysteine. Conjugates were used to immunize sheep according to the following scheme: A sheep was initially immunized with 100 μg conjugate (mass refers to the peptide moiety of the conjugate) and boostered with 50 μg thereafter in four-weekly intervals. Four months after the initial immunization 300 ml antiserum was obtained from the sheep.

Rabbit polyclonal antibodies directed against HA-AR-10 (amino acids 21-29 of histone H2A type 1, SEQ ID NO:24) and HA-IL-23 (amino acids 30-51 of histone H2A type 1, SEQ ID NO:26) were generated according to standard procedures. Briefly, peptides were coupled to KLH using MBS via an extra N-terminal cysteine. Conjugates were used to immunize rabbits according to the following scheme: A rabbit was initially immunized with 800 μg conjugate (mass refers to the peptide moiety of the conjugate) and starting in week four boostered 3-times with 500 μg thereafter in weekly intervals. Two months after the initial immunization, each 20 ml antisera were obtained from the rabbits.

Antigen-specific antibodies were purified from the respective antisera as follows: 5 mg of the purification peptide (see table 1 below) was coupled to 5 ml SulfoLink-gel (Pierce, Rockford, Ill., USA). 50 ml antiserum was incubated with the gel batchwise for 4 hours at room temperature. The suspension was transferred into a column (empty NAP25 column, GE Healthcare Life sciences). After the flow through was discarded and the column was washed with 100 ml wash buffer (100 mM KPi, 0.1% Tween-20, pH 6.8), and specifically bound antibodies were eluted with 50 mM citric acid, pH 2.7. The eluate was dialyzed against 50 mM NaPi, 100 mM NaCl, pH 8.0.

TABLE 1

Peptides used for histone H4 and histone H2A polyclonal antibody generation

| Immunization Peptide | SEQ ID NO | Screening peptide | SEQ ID NO |
|---|---|---|---|
| Histone H4 | | | |
| H4-GR-17 | 8 | H4-GH-18 | 9 |
| H4-LI-9 | 10 | H4-LI-9 | 10 |
| H4-LR-15 | 11 | H4-LL-17 | 12 |
| H4-PR-15 | 13 | H4-PS-17 | 14 |
| H4-EE-13 | 15 | H4-EN-14 | 16 |
| H4-RR-13 | 17 | H4-RK-14 | 18 |
| H4-TK-13 | 19 | H4-TR-14 | 20 |
| H4-RG-9 | 21 | H4-RG-9 | 21 |
| Histone H2A | | | |
| HA-AR-10 | 24 | HA-AH-12 | 25 |
| HA-IL-23 | 26 | HA-IA-25 | 27 |

C. Development of Monoclonal Antibodies

Monoclonal antibodies against H4-GR-17 (amino acids 2-17 of histone H4, SEQ ID NO:8), H4-LI-9 (amino acids 22-30 of histone H4, SEQ ID NO:10), H4-EE-13 (amino acids 52-63 of histone H4, SEQ ID NO:15), H4-RR-13 (amino acids 67-78 of histone H4, SEQ ID NO:17), H4-TK-13 (amino acids 80-91 of histone H4, SEQ ID NO:19), H4-RG-12 (amino acids 92-102 of histone H4, SEQ ID NO:22) and full length histone H3 (Sigma Aldrich SRP0177, SEQ ID NO:36) were generated by standard procedures (Lane, R. D. J Immunol Methods, 1985, 81(2): 223-228). In this study the exposure period of the lymphocyte-myeloma cell mixture to the fusogen was evaluated for its influence upon the yield of total hybridoma colonies and those which secreted monoclonal antibodies. Sp2/0 and FOX-NY myeloma cells were fused for varying periods with murine splenic lymphocytes immunized with sheep red blood cells. The optimal fusion period consisted of adding the fusogen (5.0 ml Kodak 1450 PEG, 0.5 ml dimethylsulfoxide, and 4.5 ml of phosphate-buffered saline, pH 7.0) to the cell mixture over a 45 s period at 37 degrees C. The fusion process was stopped by gradually diluting the mixture in 50 ml of RPMI-1640. After 10 min, the cells were centrifuged, resuspended in selective medium with feeder macrophages and cultured. In comparison to common, longer fusion techniques, this procedure produces approximately a 5-fold increase in the number of hybrids produced when using the Sp2/0 cells and a 30-fold increase in the number of hybrids produced when using the FOX-NY cells as the fusion partner. In both cases, virtually all the wells contain monoclonal antibody-secreting hybridoma colonies. This high efficiency fusion technique can be used most advantageously to produce monoclonal antibodies against weak immunogens or to reduce the time needed for immunization with stronger immunogens.

Briefly, herein, peptides were conjugated to BSA by using Sulfo-MBS (m-maleimidobenzoyl-N-hydroxysuccinimid ester). With these conjugates and histone H3 Balb/c mice were immunized and boostered, and spleen cells were fused with SP2/0 myeloma cells to generate hybridoma cell lines. Cell lines were screened for their ability to secret antibodies that bind to screening peptide (see table 2) and recombinant full length histone protein, which were coated on a solid polystyrene phase. Cell lines secreting monoclonal antibodies AK 654/F3 and 654/H10 (against H4-GR-17), AK 602/F11 and 602/G3 (against H4-LI-9) and AK 660/D2, AK 660/G9, AK 660/F6, AK 660/E9, AK 660/G3 and AK 660/F7 (against histone H3) were generated.

Furthermore, a monoclonal mouse antibody directed against a region within residues 50-102 of histone H4 was purchased from Abcam (#ab31830).

TABLE 2

Peptides used for histone H4 and histone H3 monoclonal antibody generation

| Immunization Peptide | SEQ ID NO | Screening peptide | SEQ ID NO |
|---|---|---|---|
| Histone H4 | | | |
| H4-GR-17 | 8 | H4-GH-18 | 9 |
| H4-LI-9 | 10 | H4-LI-9 | 10 |
| H4-EE-13 | 15 | H4-EN-14 | 16 |
| H4-RR-13 | 17 | H4-RK-14 | 18 |
| H4-TK-13 | 19 | H4-TR-14 | 20 |
| H4-RG-12 | 22 | H4-RG-12 | 22 |
| Histone H3 | | | |
| Rec. histone H3 | 36 | Rec. histone H3 | 36 |

D. Labeling of Antibodies

Antibodies were labeled according to standard procedures (EP 1488209 A1, EP 1738178 A1): The concentration of the respective purified antibody was adjusted to 1 g/l, and the antibody was labeled by incubation with the chemiluminescent label MACN-Acridinium-NHS-Ester (1 g/l; InVent GmbH, Hennigsdorf, Germany) in a 1:5 molar ratio for 20 min at room temperature. The reaction was stopped by addition of 1/10 volume of 50 mM glycine for 10 min at room temperature. Labeled antibody was separated from free label by size exclusion chromatography on a NAP-5 column (GE Healthcare Life sciences) and a Bio-Sil® SEC-400-5 HPLC column (Bio-Rad).

Example 2: Development of Free Histone Immunoassay

A. Coating of the Antibodies

Antibodies were coated according to standard procedures (EP 1488209 A1, EP 1738178 A1): Polystyrene startubes (Greiner) were coated with purified antibody (per tube, 2 μg of antibody in 300 μl of 10 mM Tris, 100 mM NaCl, pH 7.8) overnight at 22° C. Tubes were then blocked with 10 mM NaPi (pH 6.5) containing 30 g/l Karion F P (Merck), 5 g/l BSA protease free (Sigma Aldrich) and lyophilized.

Figure 2:
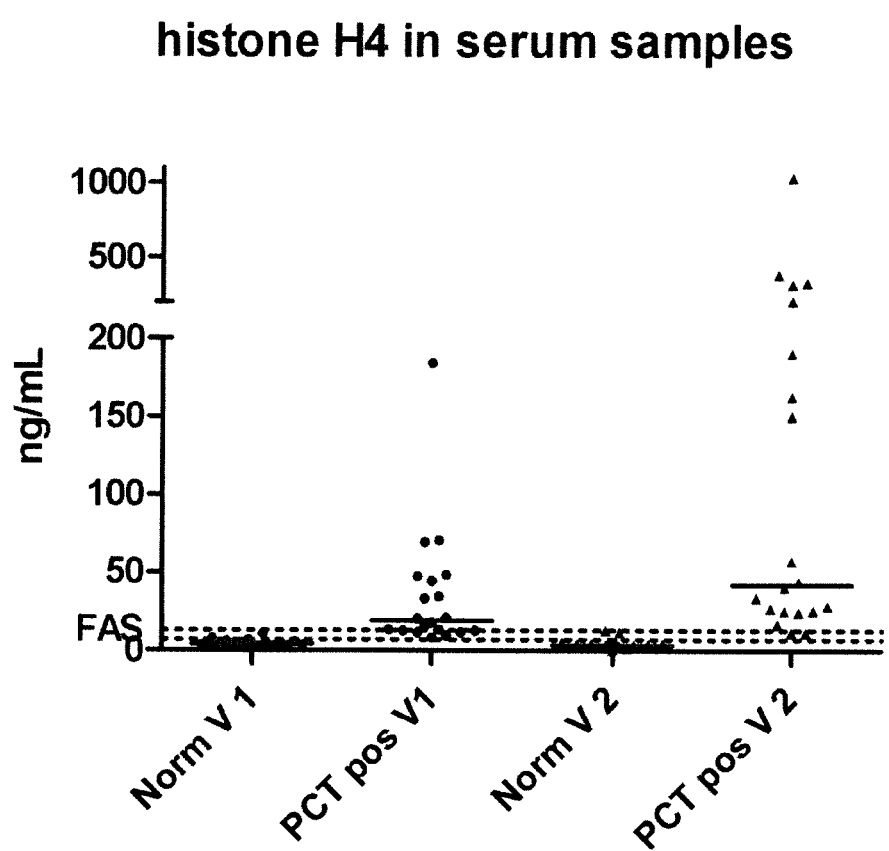
FIG. 2: Comparison of immunoassays H4-LI-9-ab31830 (V1) versus H4-RR-13-ab31830 (V2) that detect histone H4 in samples.
Figure 3:
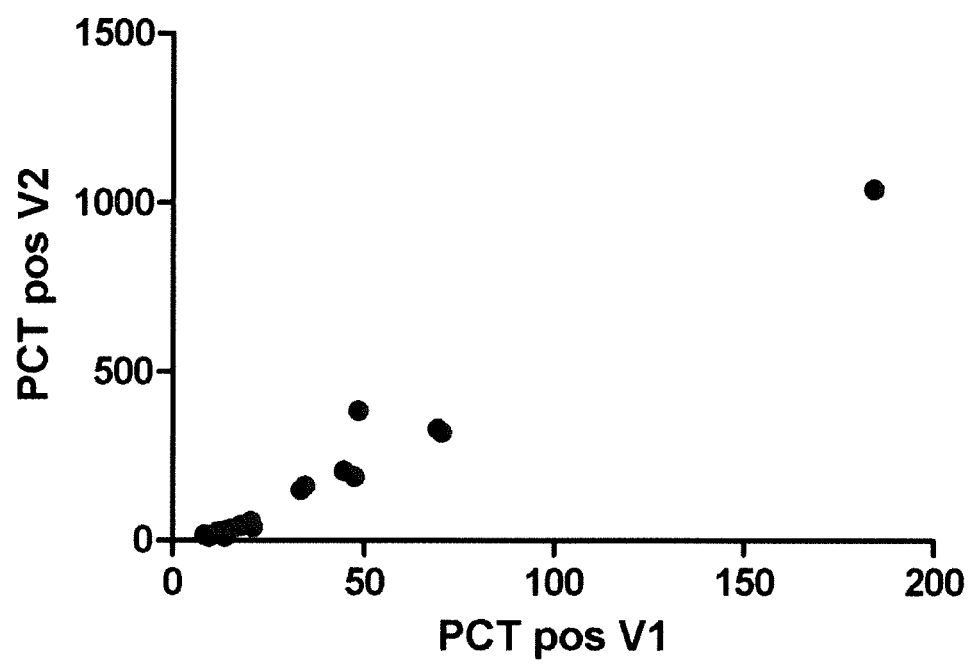
FIG. 3: Correlation of immunoassays H4-LI-9-ab31830 (V1) versus H4-RR-13-ab31830 (V2) that detect histone H4 in samples.

B. Reference Histone H4 Assay Using Poly- and Monoclonal and Commercially Available Monoclonal Antibodies Histone H4: Several sandwich histone immunoassays were set up using polyclonal and monoclonal components described above and using recombinant human full length histone H4 (Sigma Aldrich #SRP0178, SEQ ID NO:1). Best signals were observed in serum and EDTA plasma samples using the combinations using anti-H4-LI-9 (variant V1) and anti-H4-RR-13 (variant V2) coated in tubes and the Abcam anti-histone H4 ab31830 directed against residues within amino acids 50-102 of histone H4. No signal was seen in samples from healthy volunteers (signals were below the functional assay sensitivity), however, samples from patients with elevated levels of procalcitonin, suggesting a severe bacterial infection or sepsis, were all above the functional assay sensitivity (FAS) (FIG. 1). Both combinations of the assay correlated, but lower levels were measured when using the combination H4-LI-9, possibly due to proteolysis of the analyte (SEQ ID NO:1) between regions H4-LI-9 (SEQ ID NO:10) and H4-RR-13 (SEQ ID NO:17) leading to a lower concentration of longer fragments of histone H4 than of smaller C-terminal fragments (FIGS. 2 and 3).

50 µl standards (recombinant human full length histone H4 from Sigma Aldrich #SRP0178, SEQ ID NO: 1) or samples from patients and 200 µl of buffer containing the MACN-labeled antibody were mixed in the coated tubes (300 mM KPi, pH 7.0, 50 mM NaCl, 10 mM EDTA, 0.09% NaN$_3$, 0.1% BSA, 0.1% unspecific bovine IgG, 0.1% unspecific IgG, 0.01% unspecific mouse IgG), and contained 0.5×10$^6$ relative light units (RLU) of MACN-labeled antibody per 200 µl. The tubes were incubated 18-24 hours at room temperature. Then, the tubes were washed 4 times with 1 ml of B.R.A.H.M.S 50× universal washing solution (TRIS 400 mM, NaCl 3 M, Tween20 1%, Silicone defoamer 0.001% (Thermo Fisher Scientific, B.R.A.H.M.S GmbH, Hennigsdorf, Germany), and bound chemiluminescence was measured for 1 s per tube with LB925T luminometer (Berthold). Concentrations of samples were calculated using the software Multicalc (Spline Fit).

C. Dose Response Curve

Figure 4:
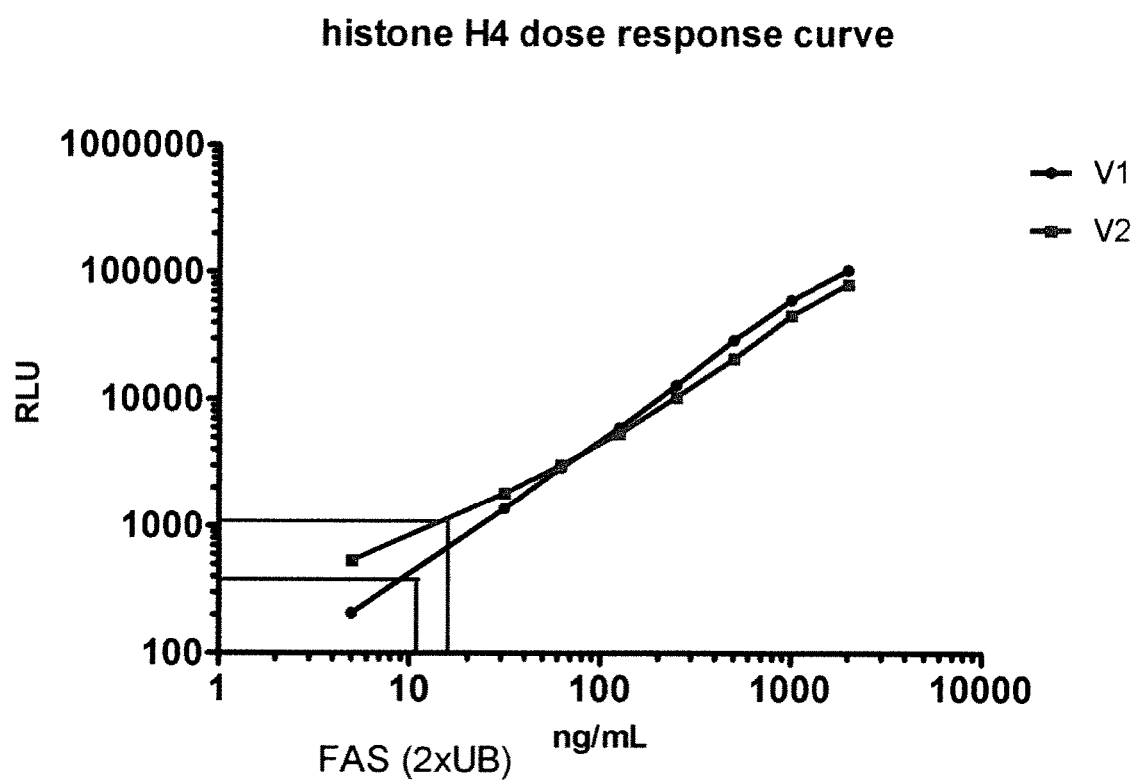
FIG. 4: Dose response curve immunoassays H4-LI-9-ab31830 (V1) versus H4-RR-13-ab31830 (V2) that detecting histone H4 in zero serum.

A dose response curve was created by using recombinant histone H4 (Sigma Aldrich #SRP0178, SEQ ID NO:1) as standard material in the two immunoassays described above. Typical dose response curves are shown in FIG. 4.

Example 3: Correlation Between SRM and Immunoassay

The very same samples that were tested in the immunoassay of the present invention were assessed with SRM assay of the present invention described herein below.

Figure 5:
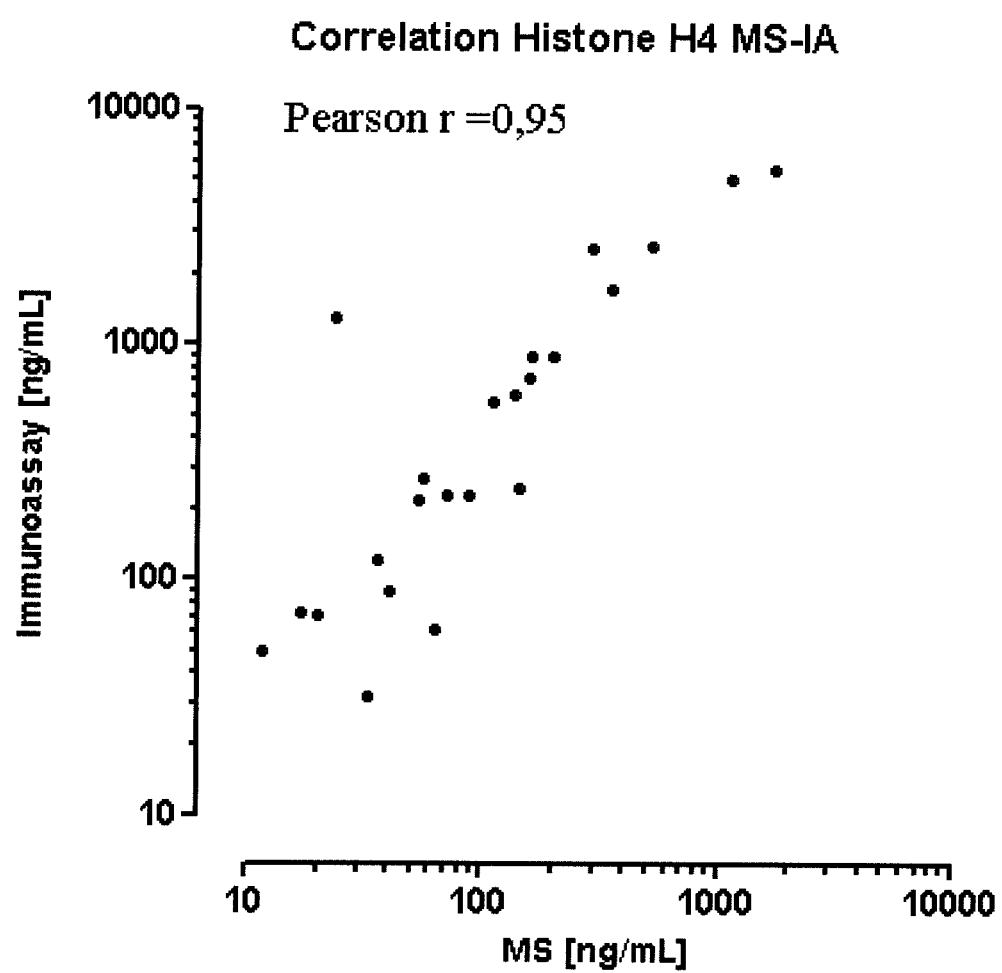
FIG. 5: Correlation between SRM and immunoassay.

FIG. 5 shows that the histone H4 LIA and the SRM assays of the present invention correlate very well with a Pearsson correlation coefficient of 0.95, indicating that both assay measure the same analyte. For the same reason that antibodies specific for residues located in the central part of histone H4 are unable to bind when the histone is complexed in an octamer, the trypsine protease is unable to reach potential cleavage sites in that region. Hence, only free histones can be cleaved at the central part and detectable peptides, such as SEQ ID NO:3 and 4, originating from that region can only be generated from free histones.

Figure 6:
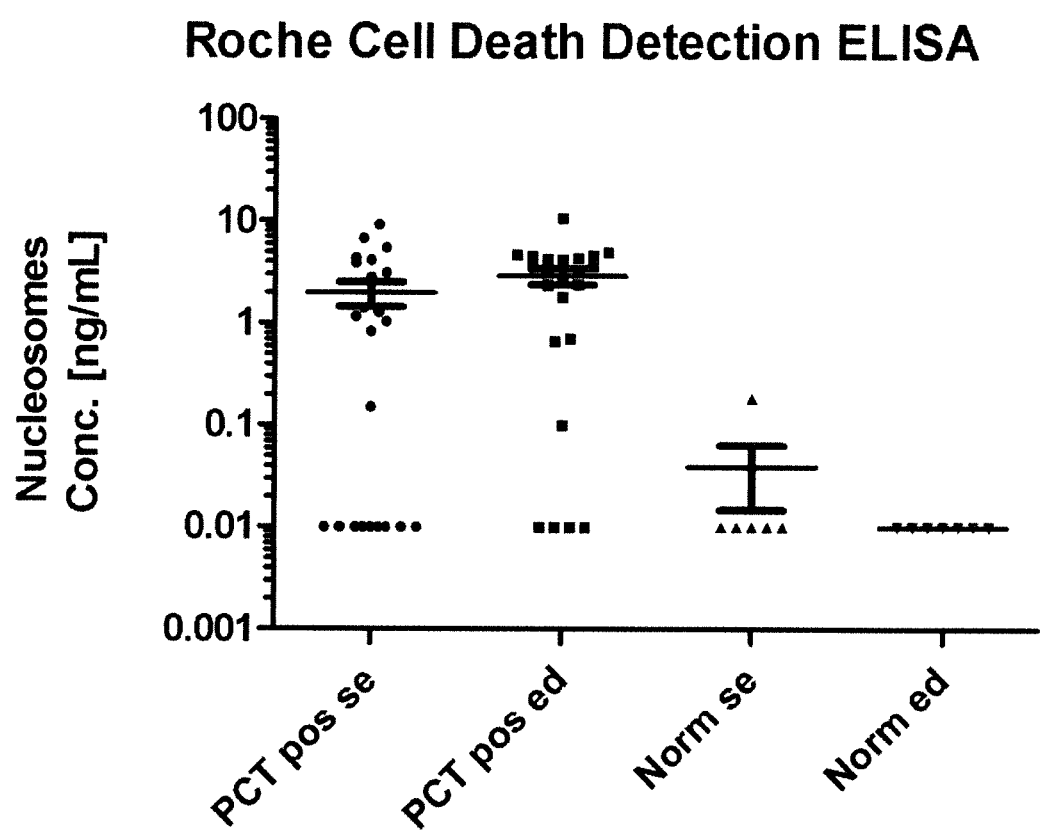
FIG. 6: Nucleosome concentration determined with the Roche Cell Death Detection ELISA (#11544675001) using the same samples as in FIG. 1.
Figure 7:
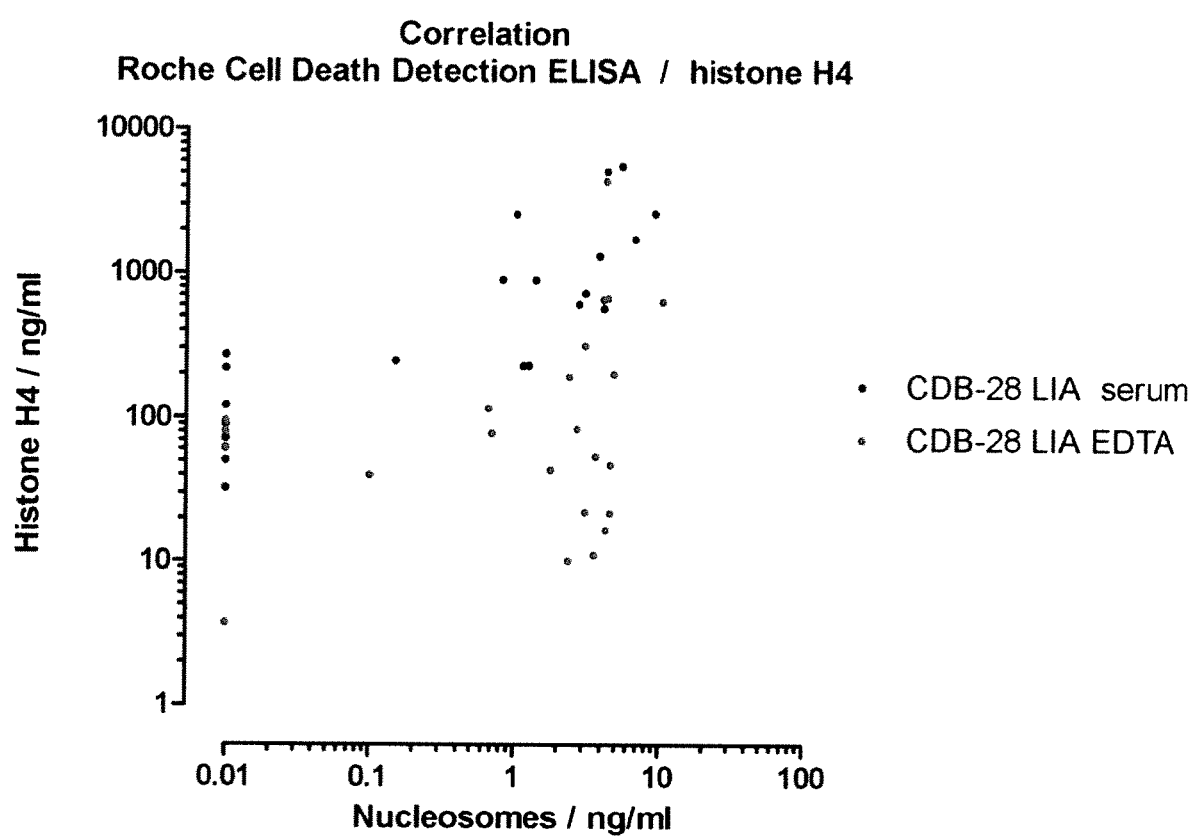
FIG. 7: Comparison between the sandwich immunoassay and the SRM assay of the present invention and the commercially available Roche Cell Death Detection ELISA (#11544675001) showing that free histone proteins but not nucleosomes are detected.

Example 4: Comparison Between the Sandwich Immunoassay and the SRM Assay of the Present Invention and a Commercially Available ELISAs from Roche that is Directed Against Nucleosomes Recombinant full length histone H4, that was used to generate the standard curve shown in FIG. 4, was tested in a commercially available ELISA system from Roche: Despite the fact that the Roche Cell Death Detection ELISA (#11544675001) is designed for specific determination of mono- and oligonucleosomes in the cytoplasmic fraction of cell lysates, we tested its performance in serum and EDTA plasma samples, because histones H2A, H2B, H3 and H4 form the octameric core of nucleosomes. The assay contains a microtiter plate coated with antibody directed against mammalian histones H2A, H2B, H3 and H4 and a detection antibody directed against DNA. Because the kit does not include standard material, we used native nucleosomes (BPS Bioscience #52015) to estimate matrix concentrations. Using the very same samples that were tested for histone H4 concentrations shown in FIG. 1, nucleosomes levels were either elevated or not detectable in patients with elevated procalcitonin levels (FIG. 6). Thus, no correlation between nucleosome and free histone H4 levels can be concluded (FIG. 7). Additionally, we tested the commercially available analytes spiked into zero serum: recombinant human histone H2A (Sigma Aldrich #SRP0406, SEQ ID NO:23), recombinant human histone H3 (Sigma Aldrich #SRP0177, SEQ ID NO:36), and histone H4 (Sigma Aldrich #SRP0178, SEQ ID NO:1), and native human nucleosomes (BPS Bioscience #52015). Table 3 lists which analytes could be detected by either the BRAHMS histone H4 LIA or the Roche Cell Death Detection ELISA. The histone H4 LIA was specific for the human histone H4, did not detect histone H2A and H3, and, importantly, did not detect native nucleosomes. This suggests that epitopes of histone H4, which are recognized by the antibodies used in the immunoassay described in the present invention, are not accessible when histone H4 is part of the octameric core of nucleosomes. However, when histone H4 is free in solution, the histone H4 LIA is able to detect histone H4 levels in matrices including serum and EDTA plasma. In contrast, the Roche Cell Death Detection ELISA detects the nucleosomes, but none of the histones.

TABLE 3

Comparison of Analyte Detection by BRAHMS Histone H4 Immunoassay vs. Roche Cell Death Kit.

| Analyte | BRAHMS Histone H4 LIA | Roche Cell Death Detection ELISA |
| --- | --- | --- |
| Rec. full length Histone H4 (Sigma SRP0178) | Yes | No |
| Rec. full length Histone H2A (Sigma SRP0406) | No | No |
| Rec. Full length Histone H3 (SigmaSRP0177) | No | No |
| Rec. Nucleosomes (BPS Bioscience 52015) | No | Yes |

Example 5: Mass Spectrometry-Based Selected Reaction Monitoring (SRM)

SRM is an MS-based technique for the targeted detection and quantification of previously selected proteotypic peptides with defined fragmentation properties detectable in a highly complex background such as blood-derived serum or plasma.

Specific peptides derived from histone H4 and histone H2A, referred to as H4 and H2A, were detected by LC-MS/MS technology (TSQ vantage mass spectrometer (MS); ThermoFisher Scientific). Discovery results were confirmed by SRM analysis showing that H4-derived peptides alter along the course of an evolving blood stream infection. Identified peptide sequences and fragmentation ions thereof, so-called transitions, for each peptide were found to be useful surrogates for monitoring H4 and H2A protein levels in a blood sample.

The quantitative SRM assay described in the following was developed to measure the relative quantitative levels of unmodified histone-derived peptides generated by tryptic digestion of plasma or serum proteins.

Optimization was done on recombinant proteins purchased from Sigma. All possible tryptic peptides were screened and best peptides regarding signal to noise were selected (see Tables 4 and 5). Optimal retention time, dwell time and collision energy for at least 4 best transitions were set up.

Figure 9:
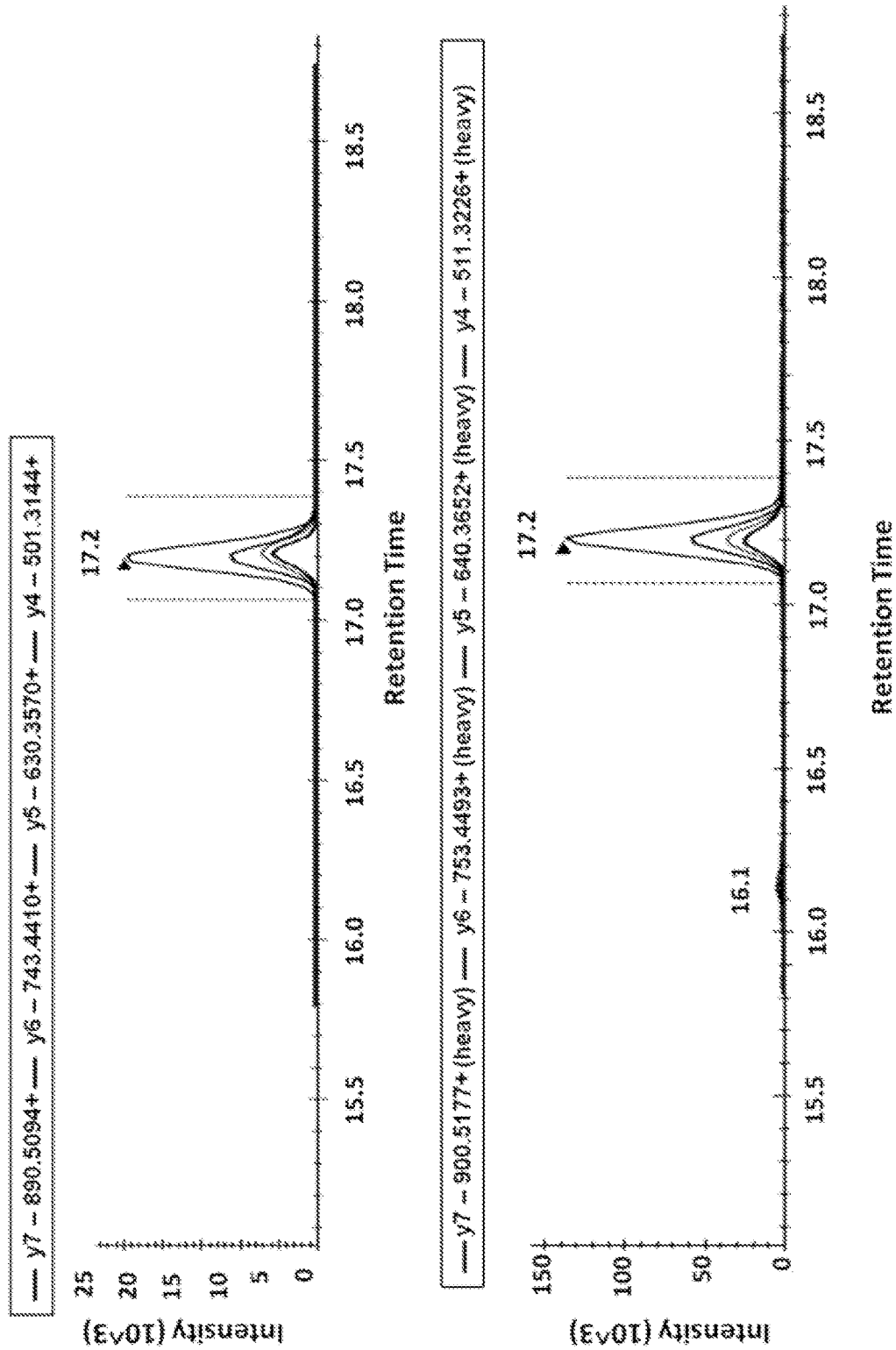
FIG. 9: SRM profile (Skyline software) for histone H4 peptide VFLENVIR (SEQ ID NO:4) in a serum sample from a patient suffering from sepsis. Top graph represents 4 transitions of endogeneous peptide. Bottom graph represents the corresponding 4 transitions of the heavy spiked peptide.

An example for peptide VFLENVIR (SEQ ID NO:4) is shown in FIG. 9.

Example 6: Setting Up of an SRM/MRM Assay for Histone Proteins

SRM/MRM Assay on a Triple Quadrupole Mass Spectrometer for Individual Fragment Peptides SRM is a MS-based technique for the targeted detection and quantification of previously selected proteotypic peptides with defined fragmentation properties detectable in a highly complex background such as blood-derived serum or plasma.

The quantitative SRM assay described in the following was developed to measure the quantitative levels of unmodified histone-derived peptides generated by tryptic digestion of plasma or serum proteins.

Specific peptides derived from histone H4 and histone H2A, referred to as H4 and H2A, were detected by LC-MS/MS technology (TSQ vantage and TSQ Quantiva mass spectrometers (MS); ThermoFisher Scientific). Identified peptide sequences and fragmentation ions thereof, so-called transitions, for each peptide were found to be useful surrogates for monitoring H4 and H2A protein levels in a blood sample.

Optimization was done on recombinant proteins purchased from Sigma. All possible tryptic peptides were screened and best peptides regarding signal to noise were selected (see Tables 4 and 5). Optimal retention time, dwell time and collision energy for at least 4 best transitions were set up.

Relative quantification and/or absolute quantification can be performed on clinical samples and assay performances were evaluated using Normal curves or Reverse curves.

Example 7: Demonstration of MS Quantification/Choice of Peptides and Transitions A. Sample Preparation Plasma samples (12 µL) were thawed on ice and mixed with 50 µL of 8 M Urea/2.5% n-propanol/200 mM Tris-HCl/10 mM DTT pH 8.5. Samples were incubated at 37° C. for 1 hour. Samples were then alkylated with 5 µL of 500 mM iodoacetic acid in 1 M ammonium bicarbonate, and incubated in the dark for 1 hour at room temperature. Residual alkylation agent was then reacted with 3.3 µL of 500 mM DTT. Samples were then diluted with 260 µL of 50 mM Tris-HCl, 5 mM $CaCl_2$) buffer pH 8. 150 µL of trypsin (Pierce, 20 µg in 25 mM acetic acid) was then added to each sample, rendering a 1:50 trypsin:protein ratio. Samples were allowed to digest for 18 hours at 37° C. For discovery runs, 300 ng of sample was loaded on a 50 mm×1 mm 1.9 µm Hypersil Gold column (ThermoFisher Scientific), prior to mass spectrometry analysis.

SRM assays were developed either on a Vantage triple quadrupole mass spectrometer, Surveyor MS pump, CTC PAL Autosampler and an IonMax Source equipped with a high flow metal needle (Thermo Fisher Scientific) or on a triple quadrupole mass spectrometer TSQ Quantiva coupled with HPLC Ultimate 3000 (Thermo Fisher Scientific). Reverse phase separations were carried out in a 20 min linear gradient from 5% to 40% B, with a total run time of 40 min (Solvent A: Water 0.2% FA (formic acid), Solvent B: ACN (acetonitrile) 0.2% FA). The flow rate during the linear gradient was set to 240 µL/min. The total injection volume was 160 µL for all samples and points on the curve. A column ACCUCORE 2.6 µM AQ 150λ2.1 mm (Thermofisher Scientific) was run at a temperature of 50° C.

5 µL of each clinical plasma sample was added to 20 µL of 8 M Urea/2.5% n-propanol/300 mM Tris-HCl/10 mM DTT pH 8.5 and incubated at 37° C. for 1 hour. 500 mM iodoacetic acid prepared in 1 M ammonium bicarbonate was added to each sample well and incubated in the dark at room temperature for 1 hour. 113 µL of 50 mM Tris-HCl/5 mM $CaCl_2$) pH 8.0 were added to each well. Trypsin (Pierce, ThermoFisher Scientific) was rehydrated with 150 µL of 25 mM acetic acid and was added with a ratio 1:10 (total protein content:protease) and incubated at 37° C. for 20 hours. Digestion was finally quenched with the additional of 2 µL of formic acid. Glucagon (1 ng/µL) and standard heavy peptides were then added before injection.

Isotopically labeled peptides C-terminal lysine or arginine were chemically synthesized and purified (>95% peptide purity, >99% isotopic purity) by Thermo Fisher Scientific GmbH, Ulm, Germany, or New England Peptide Inc, Gardner, Mass., USA.

The obtained retention time information from the discovery MS experiments was imported into Pinpoint (ThermoFisher Scientific) to build a preliminary scheduled SRM method for optimization. Individual instrument parameters such as collision energy, tube lens, dwell time and predicted retention times were automatically tested for every transition. After multiple iterations, the optimized (i.e. highest intensity signal and least overlap with other transitions) list of peptides and transitions was finalized and at least two proteotypic peptides per protein and at least four fragment transitions per peptide were chosen.

Tables 4 and 5 list all peptides analyzed for human H4 and H2A proteins. A total of 6 peptides were screened for histone H4 and 6 peptides for histone H2A.

Regarding histone H4, transitions analysis was performed in detail for 5 peptides. Peptides according to SEQ ID NOs:3 and 4 were analyzed as heavy-labeled peptides and 4 to 5 transitions were monitored for each peptide.

Regarding histone H2A, transitions analysis was performed in detail for 4 peptides. Peptides according to SEQ ID NOs:24 and 28 were analyzed as heavy-labeled peptides and 4 to 5 transitions were monitored for each peptide.

Peptides were identified by co-eluting light and heavy-labeled transitions in the chromatographic separation. Pinpoint software (Thermo Fisher Scientific) or Skyline software (open source) were used for time alignment, relative quantification of the transitions and targeted protein quantification.

TABLE 4

Example Peptides and transitions monitored for H4.

| SEQ ID NO | Peptide sequence | Precursor m/z | Fragment m/z | Precursor charge state | Fragment charge state | Fragment Ion Type |
|---|---|---|---|---|---|---|
| 3 | ISGLIYEETR | 590.814 | 697.315 | 2 | 1 | y5 |
| 3 | ISGLIYEETR | 590.814 | 810.399 | 2 | 1 | y6 |
| 3 | ISGLIYEETR | 590.814 | 980.504 | 2 | 1 | y8 |
| 3 | ISGLIYEETR | 590.814 | 1067.536 | 2 | 1 | y9 |
| 3 | ISGLIYEETR | 590.814 | 534.251 | 2 | 1 | y4 |
| 4 | VFLENVIR | 495.293 | 387.271 | 2 | 1 | y3 |
| 4 | VFLENVIR | 495.293 | 501.314 | 2 | 1 | y4 |
| 4 | VFLENVIR | 495.293 | 630.356 | 2 | 1 | y5 |
| 4 | VFLENVIR | 495.293 | 743.441 | 2 | 1 | y6 |
| 4 | VFLENVIR | 495.293 | 890.509 | 2 | 1 | y7 |
| 5 | TVTAMDVVYALK | 655.855 | 807.461 | 2 | 1 | y7 |
| 5 | TVTAMDVVYALK | 655.855 | 938.501 | 2 | 1 | y8 |
| 5 | TVTAMDVVYALK | 655.855 | 1009.538 | 2 | 1 | y9 |
| 5 | TVTAMDVVYALK | 655.855 | 1110.586 | 2 | 1 | y10 |
| 6 | DNIQGITKPAIR | 442.589 | 456.292 | 3 | 1 | y4 |
| 6 | DNIQGITKPAIR | 442.589 | 584.387 | 3 | 1 | y5 |
| 6 | DNIQGITKPAIR | 442.589 | 685.435 | 3 | 1 | y6 |
| 6 | DNIQGITKPAIR | 442.589 | 428.274 | 3 | 2 | y8 |
| 7 | DAVTYTEHAK | 567.775 | 585.299 | 2 | 1 | y5 |
| 7 | DAVTYTEHAK | 567.775 | 748.362 | 2 | 1 | y6 |
| 7 | DAVTYTEHAK | 567.775 | 849.410 | 2 | 1 | y7 |
| 7 | DAVTYTEHAK | 567.775 | 474.743 | 2 | 2 | y8 |

TABLE 5

Example Peptides and transitions monitored for H2A.

| SEQ ID NO | Peptide sequence | Precursor m/z | Fragment m/z | Precursor charge state | Fragment charge state | Fragment Ion Type |
|---|---|---|---|---|---|---|
| 24 | AGLQFPVGR | 472.769 | 428.261 | 2 | 1 | y4 |
| 24 | AGLQFPVGR | 472.769 | 575.330 | 2 | 1 | y5 |
| 24 | AGLQFPVGR | 472.769 | 703.388 | 2 | 1 | y6 |
| 24 | AGLQFPVGR | 472.769 | 816.472 | 2 | 1 | y7 |
| 24 | AGLQFPVGR | 472.769 | 408.740 | 2 | 2 | y7 |
| 28 | HLQLAIR | 425.767 | 472.324 | 2 | 1 | y4 |
| 28 | HLQLAIR | 425.767 | 600.382 | 2 | 1 | y5 |
| 28 | HLQLAIR | 425.767 | 713.466 | 2 | 1 | y6 |
| 28 | HLQLAIR | 425.767 | 563.330 | 2 | 1 | b4 |
| 29 | NDEELNK | 431.201 | 503.282 | 2 | 1 | y4 |
| 29 | NDEELNK | 431.201 | 632.325 | 2 | 1 | y5 |
| 29 | NDEELNK | 431.201 | 747.351 | 2 | 1 | y6 |
| 29 | NDEELNK | 431.201 | 601.246 | 2 | 1 | b4 |
| 30 | VTIAQGGVLPNIQAVLLPK | 644.394 | 470.333 | 3 | 1 | y4 |
| 30 | VTIAQGGVLPNIQAVLLPK | 644.394 | 1205.761 | 3 | 1 | y11 |
| 30 | VTIAQGGVLPNIQAVLLPK | 644.394 | 1361.851 | 3 | 1 | y13 |
| 30 | VTIAQGGVLPNIQAVLLPK | 644.394 | 435.615 | 3 | 3 | y12 |

B. MS Analysis

SRM/MRM analysis was performed so that the amount of the fragment peptide of the histone proteins that is detected, as a function of the unique SRM/MRM signature peak area from an SRM/MRM mass spectrometry analysis, indicates both the relative and absolute amount of the protein in a particular sample.

Example 8: Calibration Curve Generation to Evaluate Sensitivity

A constant amount of light peptide was spiked on top of the endogenous analyte to create an internal standard and varying amounts of heavy peptide are spiked to create a set of concentration standards. Because the varying heavy peptide signal used to create the curve is not contributed to by an unknown amount of endogenous analyte, it is possible to determine the limit of quantification (LOQ) values, referring to the point where measurements become quantitatively meaningful. The analyte response at this LOQ is identifiable, discrete and reproducible with a precision of 20% and an accuracy of 80-120%.

Reverse Calibration curves were created with a pool of plasma samples as a background matrix. Each point on the calibration curve (and every sample analyzed) included 100 fmol of heavy labeled peptides. The amount of background matrix on column was 20 µg for each point on the calibration curve, as well as in all analyzed samples. Heavy standard peptides (Isotopically labeled peptides C-terminal lysine or arginine chemically synthesized and purified >95% peptide purity, >99% isotopic purity by Thermo Fisher Scientific GmbH, Ulm, Germany, or New England Peptide Inc, Gardner, Mass., USA) were spiked after digestion. In addition, all samples were brought up in a solution of 1 µg/mL of glucagon in Water/0.2% FA to minimize binding to plastic surfaces.

Figure 10:
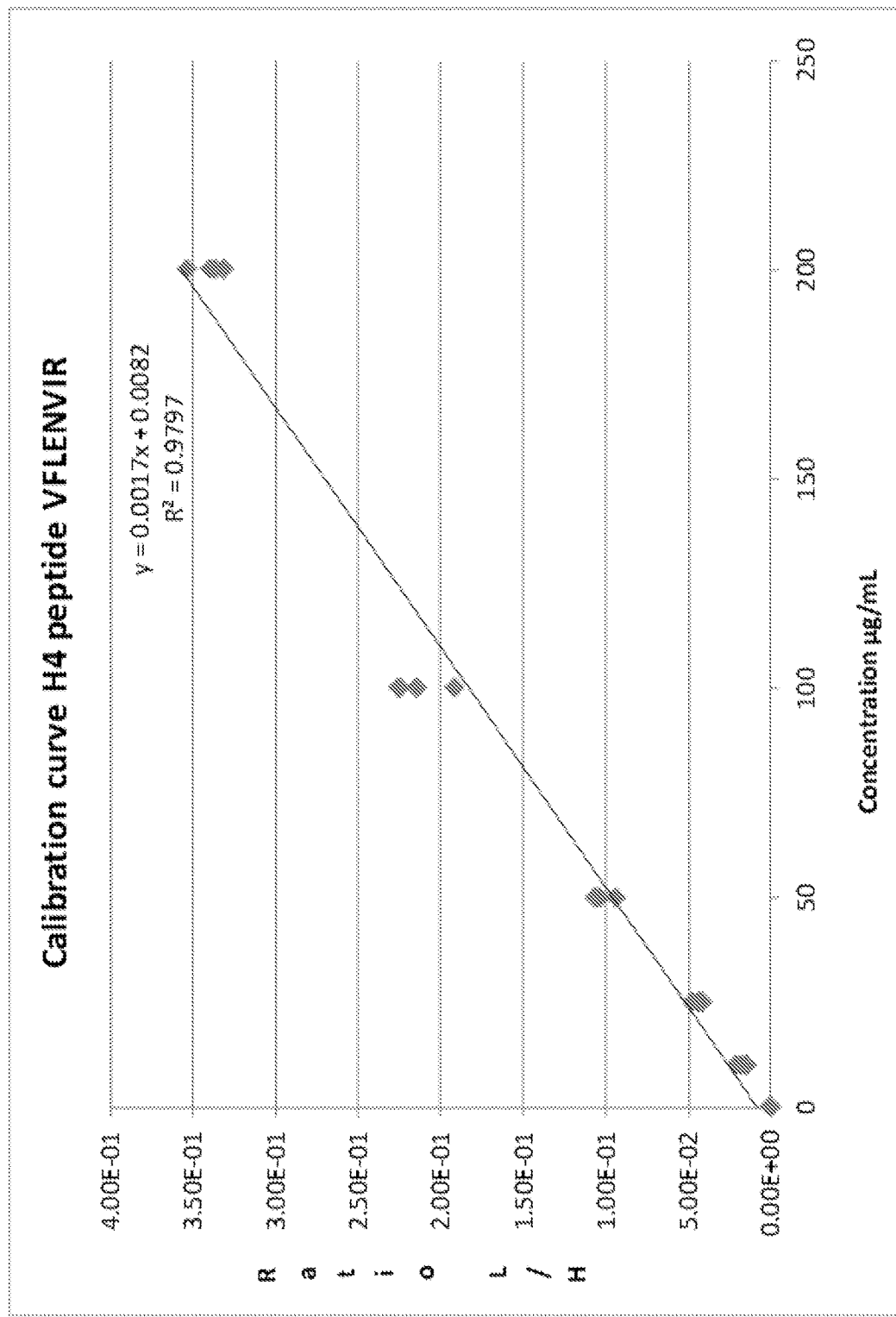
FIG. 10: Calibration curve of peptide VFLENVIR (SEQ ID NO:4) from histone H4. Constant amount of light peptide obtained from recombinant H4 digestion, and varying amount of corresponding heavy peptide are spiked to create a set of concentration standards.

FIG. 10 illustrates a calibration curve of peptide VFLEN-VIR (SEQ ID NO:4) from histone H4. Constant amount of light peptide obtained from recombinant H4 digestion, and varying amount of corresponding heavy peptide are spiked to create a set of concentration standards.

Example 9: Relative Quantification rSRM on Human Dataset

SRM/MRM analysis was performed so that the amount of the fragment peptide of the histone proteins that is detected, as a function of the unique SRM/MRM signature peak area from an SRM/MRM mass spectrometry analysis, indicates both the relative and absolute amount of the protein in a particular protein lysate.

Relative quantification rSRM may be achieved by:

1. Determining increased or decreased presence of the histone proteins by comparing the SRM signature peak area from a given histone peptide detected in biological sample to the same SRM signature peak area of the same histone fragment peptide in at least a second, third, fourth or more biological samples 2. Determining increased or decreased presence of histone proteins by comparing the SRM signature peak area from a given histone peptide detected in a biological sample to SRM signature peak areas developed from fragment peptides from other proteins, in other samples derived from different and separate biological sources, where the SRM signature peak area comparison between the 2 samples for a peptide fragment are normalized for e.g. to amount of protein analyzed in each sample.

3. Determining increased or decreased presence of the histone protein by comparing the SRM signature peak area for a given histone peptide to the SRM signature peak areas from other fragment peptides derived from different proteins within the same biological sample in order to normalize changing levels of histone proteins to levels of other proteins that do not change their levels of expression under various cellular conditions.

4. These assays can be applied to both unmodified fragment peptides and for modified fragment peptides of the histone proteins, where the modifications include, but are not limited to, phosphorylation and/or glycosylation, acetylation, methylation (mono, di, tri), citrullination, ubiquitinylation, and sumoylation and where the relative levels of modified peptides are determined in the same manner as determining relative amounts of unmodified peptides.

Relative quantification rSRM was achieved by determining increased or decreased presence of the histone proteins by comparing the SRM signature peak area from a given histone peptide detected in biological sample to the same SRM signature peak area of the same histone fragment peptide in at least a second, third, fourth or more biological samples; see FIG. 9.

Absolute quantification of a given peptide may be achieved by:

Comparing the SRM/MRM signature peak area for a given fragment peptide from the histone proteins in an individual biological sample to the SRM/MRM signature peak area of an internal fragment peptide standard spiked into the protein lysate from the biological sample.

The internal standard may be a labeled synthetic version of the fragment peptide from the histone proteins that is being interrogated or the labeled recombinant protein. This standard is spiked into a sample in known amounts before (mandatory for the recombinant protein) or after digestion, and the SRM/MRM signature peak area can be determined for both the internal fragment peptide standard and the native fragment peptide in the biological sample separately, followed by comparison of both peak areas.

This can be applied to unmodified fragment peptides and modified fragment peptides, where the modifications include but are not limited to phosphorylation and/or glycosylation, acetylation, methylation (mono, di, tri), citrullination, ubiquitinylation, and where the absolute levels of modified peptides can be determined in the same manner as determining absolute levels of unmodified peptides.

Figure 8:
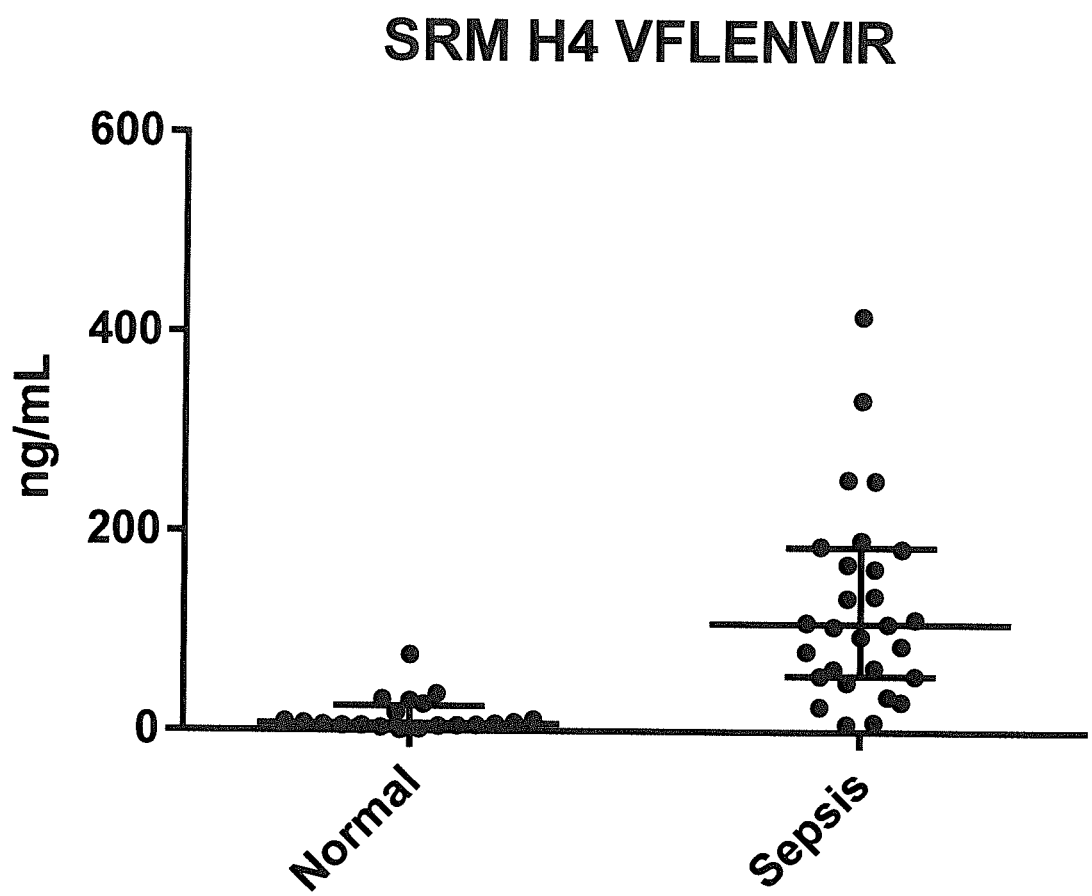
FIG. 8: Result of concentrations of histone H4 determined in serum samples from healthy volunteers and samples from patients suffering from sepsis by SRM measurement of peptide VFLENVIR (SEQ ID NO:4).

FIG. 8 shows the result of concentrations of histone H4 determined in serum samples from 20 healthy volunteers and 29 samples from patients suffering from sepsis by the SRM measurement of peptide VFLENVIR (SEQ ID NO:4).

The invention claimed is:

1. A method for detecting a free histone H4 protein or peptide fragment thereof in a biological sample of a subject comprising an immunoassay method comprising:
   (a) screening antibodies that specifically bind free H4 protein, the screening comprising:
      (i) conjugating a peptide comprising residues 22 to 30, 67 to 78, or 92 to 102 of the histone H4 protein of SEQ ID NO: 1 to bovine serum albumin (BSA);
      (ii) immunizing and boosting H3 Balb/c mice with the peptide conjugate of (i);
      (iii) harvesting spleen cells and fusing the spleen cells with SP2/0 myeloma cells to generate hybridoma cell lines;
      (iv) screening the hybridoma cell lines for cells that secrete antibodies that bind both a peptide selected from the group consisting of SEQ ID NO: 10, SEQ ID NO: 17, and SEQ ID NO: 22, and recombinant full length full-length histone protein of SEQ ID NO: 1;
      (v) harvesting antibodies from the hybridoma cell lines selected in (iv) to select and obtain a first and second antibodies that specifically bind an epitope selected form the group consisting of SEQ ID NO's 10, 17, 22 and a peptide fragment thereof, wherein the epitope is not accessible when the histone H4 protein is assembled in a nucleosome, wherein the amino acid residues in the epitope are not phosphorylated;
   (b) obtaining a sample from the subject, wherein the sample is a blood sample, serum sample, or plasma sample;
   (c) contacting the sample with the first and second antibody or an antigen-binding fragment thereof specific for a first and second epitope of the free histone protein, respectively, wherein the first and second epitope are different from each other; and
   (d) detecting the binding of the two antibodies or antigen-binding fragments thereof to the free histone H4 protein.

* * * * *

SEQUENCE LISTING

```
<160> NUMBER OF SEQ ID NOS: 41

<210> SEQ ID NO 1
<211> LENGTH: 102
<212> TYPE: PRT
<213> ORGANISM: Homo sapiens
<220> FEATURE:
<221> NAME/KEY: MISC_FEATURE
<222> LOCATION: (1)..(102)
<223> OTHER INFORMATION: amino acid sequence of human histone H4,
      uniprot ID P62805.2, initial methionine not included

<400> SEQUENCE: 1

Ser Gly Arg Gly Lys Gly Gly Lys Gly Leu Gly Lys Gly Gly Ala Lys
1               5                   10                  15

Arg His Arg Lys Val Leu Arg Asp Asn Ile Gln Gly Ile Thr Lys Pro
            20                  25                  30

Ala Ile Arg Arg Leu Ala Arg Arg Gly Gly Val Lys Arg Ile Ser Gly
        35                  40                  45

Leu Ile Tyr Glu Glu Thr Arg Gly Val Leu Lys Val Phe Leu Glu Asn
    50                  55                  60
```

```
Val Ile Arg Asp Ala Val Thr Tyr Thr Glu His Ala Lys Arg Lys Thr
65                  70                  75                  80

Val Thr Ala Met Asp Val Val Tyr Ala Leu Lys Arg Gln Gly Arg Thr
                85                  90                  95

Leu Tyr Gly Phe Gly Gly
            100

<210> SEQ ID NO 2
<211> LENGTH: 57
<212> TYPE: PRT
<213> ORGANISM: Artificial Sequence
<220> FEATURE:
<223> OTHER INFORMATION: amino acid sequence of 46-102 of SEQ ID NO: 1

<400> SEQUENCE: 2

Ile Ser Gly Leu Ile Tyr Glu Glu Thr Arg Gly Val Leu Lys Val Phe
1               5                   10                  15

Leu Glu Asn Val Ile Arg Asp Ala Val Thr Tyr Thr Glu His Ala Lys
            20                  25                  30

Arg Lys Thr Val Thr Ala Met Asp Val Val Tyr Ala Leu Lys Arg Gln
        35                  40                  45

Gly Arg Thr Leu Tyr Gly Phe Gly Gly
    50                  55

<210> SEQ ID NO 3
<211> LENGTH: 10
<212> TYPE: PRT
<213> ORGANISM: Artificial Sequence
<220> FEATURE:
<223> OTHER INFORMATION: amino acid sequence 46-55 of SEQ ID NO: 1

<400> SEQUENCE: 3

Ile Ser Gly Leu Ile Tyr Glu Glu Thr Arg
1               5                   10

<210> SEQ ID NO 4
<211> LENGTH: 8
<212> TYPE: PRT
<213> ORGANISM: Artificial Sequence
<220> FEATURE:
<223> OTHER INFORMATION: amino acid sequence 60-67 of SEQ ID NO: 1

<400> SEQUENCE: 4

Val Phe Leu Glu Asn Val Ile Arg
1               5

<210> SEQ ID NO 5
<211> LENGTH: 12
<212> TYPE: PRT
<213> ORGANISM: Artificial Sequence
<220> FEATURE:
<223> OTHER INFORMATION: amino acid sequence 80-91 with acetylated K90
      of SEQ ID NO: 1
<220> FEATURE:
<221> NAME/KEY: MOD_RES
<222> LOCATION: (12)..(12)
<223> OTHER INFORMATION: ACETYLATION

<400> SEQUENCE: 5

Thr Val Thr Ala Met Asp Val Val Tyr Ala Leu Lys
1               5                   10

<210> SEQ ID NO 6
<211> LENGTH: 12
```

```
<212> TYPE: PRT
<213> ORGANISM: Artificial Sequence
<220> FEATURE:
<223> OTHER INFORMATION: amino acid sequence 24-35 of SEQ ID NO: 1

<400> SEQUENCE: 6

Asp Asn Ile Gln Gly Ile Thr Lys Pro Ala Ile Arg
1               5                   10

<210> SEQ ID NO 7
<211> LENGTH: 10
<212> TYPE: PRT
<213> ORGANISM: Artificial Sequence
<220> FEATURE:
<223> OTHER INFORMATION: amino acid sequence 68-77 of SEQ ID NO: 1

<400> SEQUENCE: 7

Asp Ala Val Thr Tyr Thr Glu His Ala Lys
1               5                   10

<210> SEQ ID NO 8
<211> LENGTH: 16
<212> TYPE: PRT
<213> ORGANISM: Artificial Sequence
<220> FEATURE:
<223> OTHER INFORMATION: amino acid sequence of H4-GR-17, position 2-17
      of SEQ ID NO:1

<400> SEQUENCE: 8

Gly Arg Gly Lys Gly Gly Lys Gly Leu Gly Lys Gly Gly Ala Lys Arg
1               5                   10                  15

<210> SEQ ID NO 9
<211> LENGTH: 17
<212> TYPE: PRT
<213> ORGANISM: Artificial Sequence
<220> FEATURE:
<223> OTHER INFORMATION: amino acid sequence of H4-GH-18, position 2-18
      of SEQ ID NO:1

<400> SEQUENCE: 9

Gly Arg Gly Lys Gly Gly Lys Gly Leu Gly Lys Gly Gly Ala Lys Arg
1               5                   10                  15

His

<210> SEQ ID NO 10
<211> LENGTH: 9
<212> TYPE: PRT
<213> ORGANISM: Artificial Sequence
<220> FEATURE:
<223> OTHER INFORMATION: amino acid sequence of H4-LI-9, position 22-30
      of SEQ ID NO:1

<400> SEQUENCE: 10

Leu Arg Asp Asn Ile Gln Gly Ile Thr
1               5

<210> SEQ ID NO 11
<211> LENGTH: 14
<212> TYPE: PRT
<213> ORGANISM: Artificial Sequence
<220> FEATURE:
<223> OTHER INFORMATION: amino acid sequence of H4-LR-15, position 22-35
      of SEQ ID NO:1
```

<400> SEQUENCE: 11

Leu Arg Asp Asn Ile Gln Gly Ile Thr Lys Pro Ala Ile Arg
1               5                   10

<210> SEQ ID NO 12
<211> LENGTH: 16
<212> TYPE: PRT
<213> ORGANISM: Artificial Sequence
<220> FEATURE:
<223> OTHER INFORMATION: amino acid sequence of H4-LL-17, position 22-37
      of SEQ ID NO:1

<400> SEQUENCE: 12

Leu Arg Asp Asn Ile Gln Gly Ile Thr Lys Pro Ala Ile Arg Arg Leu
1               5                   10                  15

<210> SEQ ID NO 13
<211> LENGTH: 14
<212> TYPE: PRT
<213> ORGANISM: Artificial Sequence
<220> FEATURE:
<223> OTHER INFORMATION: amino acid sequence of H4-PR-15, position 32-45
      of SEQ ID NO:1

<400> SEQUENCE: 13

Pro Ala Ile Arg Arg Leu Ala Arg Arg Gly Gly Val Lys Arg
1               5                   10

<210> SEQ ID NO 14
<211> LENGTH: 16
<212> TYPE: PRT
<213> ORGANISM: Artificial Sequence
<220> FEATURE:
<223> OTHER INFORMATION: amino acid sequence of H4-PS-17, position 32-47
      of SEQ ID NO:1

<400> SEQUENCE: 14

Pro Ala Ile Arg Arg Leu Ala Arg Arg Gly Gly Val Lys Arg Ile Ser
1               5                   10                  15

<210> SEQ ID NO 15
<211> LENGTH: 12
<212> TYPE: PRT
<213> ORGANISM: Artificial Sequence
<220> FEATURE:
<223> OTHER INFORMATION: amino acid sequence of H4-EE-13, position 52-63
      of SEQ ID NO:1

<400> SEQUENCE: 15

Glu Glu Thr Arg Gly Val Leu Lys Val Phe Leu Glu
1               5                   10

<210> SEQ ID NO 16
<211> LENGTH: 13
<212> TYPE: PRT
<213> ORGANISM: Artificial Sequence
<220> FEATURE:
<223> OTHER INFORMATION: amino acid sequence of H4-EN-14, position 52-64
      of SEQ ID NO:1

<400> SEQUENCE: 16

Glu Glu Thr Arg Gly Val Leu Lys Val Phe Leu Glu Asn
1               5                   10

<210> SEQ ID NO 17
<211> LENGTH: 12

```
<212> TYPE: PRT
<213> ORGANISM: Artificial Sequence
<220> FEATURE:
<223> OTHER INFORMATION: amino acid sequence of H4-RR-13, position 67-78
      of SEQ ID NO:1

<400> SEQUENCE: 17

Arg Asp Ala Val Thr Tyr Thr Glu His Ala Lys Arg
1               5                   10

<210> SEQ ID NO 18
<211> LENGTH: 13
<212> TYPE: PRT
<213> ORGANISM: Artificial Sequence
<220> FEATURE:
<223> OTHER INFORMATION: amino acid sequence of H4- RK-14, position
      67-79 of SEQ ID NO:1

<400> SEQUENCE: 18

Arg Asp Ala Val Thr Tyr Thr Glu His Ala Lys Arg Lys
1               5                   10

<210> SEQ ID NO 19
<211> LENGTH: 12
<212> TYPE: PRT
<213> ORGANISM: Artificial Sequence
<220> FEATURE:
<223> OTHER INFORMATION: amino acid sequence of H4-TK-13, position 80-91
      of SEQ ID NO:1

<400> SEQUENCE: 19

Thr Val Thr Ala Met Asp Val Val Tyr Ala Leu Lys
1               5                   10

<210> SEQ ID NO 20
<211> LENGTH: 13
<212> TYPE: PRT
<213> ORGANISM: Artificial Sequence
<220> FEATURE:
<223> OTHER INFORMATION: amino acid sequence of H4-TR-14, position 80-92
      of SEQ ID NO:1

<400> SEQUENCE: 20

Thr Val Thr Ala Met Asp Val Val Tyr Ala Leu Lys Arg
1               5                   10

<210> SEQ ID NO 21
<211> LENGTH: 8
<212> TYPE: PRT
<213> ORGANISM: Artificial Sequence
<220> FEATURE:
<223> OTHER INFORMATION: amino acid sequence of H4-RG-9, position 92-99
      of SEQ ID NO:1

<400> SEQUENCE: 21

Arg Gln Gly Arg Thr Leu Tyr Gly
1               5

<210> SEQ ID NO 22
<211> LENGTH: 11
<212> TYPE: PRT
<213> ORGANISM: Artificial Sequence
<220> FEATURE:
<223> OTHER INFORMATION: amino acid sequence of H4-RG-12, position
      92-102 of SEQ ID NO:1
```

```
<400> SEQUENCE: 22

Arg Gln Gly Arg Thr Leu Tyr Gly Phe Gly Gly
1               5                   10

<210> SEQ ID NO 23
<211> LENGTH: 130
<212> TYPE: PRT
<213> ORGANISM: Homo sapiens
<220> FEATURE:
<221> NAME/KEY: MISC_FEATURE
<222> LOCATION: (1)..(130)
<223> OTHER INFORMATION: amino acid sequence of human histone H2A type
      1, uniprot ID Q96QV6, initial methionine not included

<400> SEQUENCE: 23

Ser Gly Arg Gly Lys Gln Gly Gly Lys Ala Arg Ala Lys Ser Lys Ser
1               5                   10                  15

Arg Ser Ser Arg Ala Gly Leu Gln Phe Pro Val Gly Arg Ile His Arg
            20                  25                  30

Leu Leu Arg Lys Gly Asn Tyr Ala Glu Arg Ile Gly Ala Gly Ala Pro
        35                  40                  45

Val Tyr Leu Ala Ala Val Leu Glu Tyr Leu Thr Ala Glu Ile Leu Glu
    50                  55                  60

Leu Ala Gly Asn Ala Ser Arg Asp Asn Lys Lys Thr Arg Ile Ile Pro
65                  70                  75                  80

Arg His Leu Gln Leu Ala Ile Arg Asn Asp Glu Glu Leu Asn Lys Leu
                85                  90                  95

Leu Gly Gly Val Thr Ile Ala Gln Gly Gly Val Leu Pro Asn Ile Gln
            100                 105                 110

Ala Val Leu Leu Pro Lys Lys Thr Glu Ser His His His Lys Ala Gln
        115                 120                 125

Ser Lys
    130

<210> SEQ ID NO 24
<211> LENGTH: 9
<212> TYPE: PRT
<213> ORGANISM: Artificial Sequence
<220> FEATURE:
<223> OTHER INFORMATION: amino acid sequence of HA-AR-10, position 21-29
      of SEQ ID NO:23

<400> SEQUENCE: 24

Ala Gly Leu Gln Phe Pro Val Gly Arg
1               5

<210> SEQ ID NO 25
<211> LENGTH: 11
<212> TYPE: PRT
<213> ORGANISM: Artificial Sequence
<220> FEATURE:
<223> OTHER INFORMATION: amino acid sequence of HA-AH-12, position 21-31
      of SEQ ID NO:23

<400> SEQUENCE: 25

Ala Gly Leu Gln Phe Pro Val Gly Arg Ile His
1               5                   10

<210> SEQ ID NO 26
<211> LENGTH: 22
<212> TYPE: PRT
<213> ORGANISM: Artificial Sequence
```

```
<220> FEATURE:
<223> OTHER INFORMATION: amino acid sequence of HA-IL-23, position 30-51
      of SEQ ID NO:23

<400> SEQUENCE: 26

Ile His Arg Leu Leu Arg Lys Gly Asn Tyr Ala Glu Arg Ile Gly Ala
1               5                   10                  15

Gly Ala Pro Val Tyr Leu
            20

<210> SEQ ID NO 27
<211> LENGTH: 24
<212> TYPE: PRT
<213> ORGANISM: Artificial Sequence
<220> FEATURE:
<223> OTHER INFORMATION: amino acid sequence of HA-IA-25, position 30-53
      of SEQ ID NO:23

<400> SEQUENCE: 27

Ile His Arg Leu Leu Arg Lys Gly Asn Tyr Ala Glu Arg Ile Gly Ala
1               5                   10                  15

Gly Ala Pro Val Tyr Leu Ala Ala
            20

<210> SEQ ID NO 28
<211> LENGTH: 7
<212> TYPE: PRT
<213> ORGANISM: Artificial Sequence
<220> FEATURE:
<223> OTHER INFORMATION: amino acid sequence 82-88 of SEQ ID NO:23

<400> SEQUENCE: 28

His Leu Gln Leu Ala Ile Arg
1               5

<210> SEQ ID NO 29
<211> LENGTH: 7
<212> TYPE: PRT
<213> ORGANISM: Artificial Sequence
<220> FEATURE:
<223> OTHER INFORMATION: amino acid sequence 89-95 of SEQ ID NO:23

<400> SEQUENCE: 29

Asn Asp Glu Glu Leu Asn Lys
1               5

<210> SEQ ID NO 30
<211> LENGTH: 19
<212> TYPE: PRT
<213> ORGANISM: Artificial Sequence
<220> FEATURE:
<223> OTHER INFORMATION: amino acid sequence 100-118 of SEQ ID NO:23

<400> SEQUENCE: 30

Val Thr Ile Ala Gln Gly Gly Val Leu Pro Asn Ile Gln Ala Val Leu
1               5                   10                  15

Leu Pro Lys

<210> SEQ ID NO 31
<211> LENGTH: 126
<212> TYPE: PRT
<213> ORGANISM: Homo sapiens
<220> FEATURE:
<221> NAME/KEY: MISC_FEATURE
<222> LOCATION: (1)..(126)
```

<223> OTHER INFORMATION: acid sequence of human histone H2B, uniprot ID
     P62807

<400> SEQUENCE: 31

Met Pro Glu Pro Ala Lys Ser Ala Pro Ala Pro Lys Lys Gly Ser Lys
1               5                   10                  15

Lys Ala Val Thr Lys Ala Gln Lys Lys Asp Gly Lys Lys Arg Lys Arg
            20                  25                  30

Ser Arg Lys Glu Ser Tyr Ser Val Tyr Val Tyr Lys Val Leu Lys Gln
        35                  40                  45

Val His Pro Asp Thr Gly Ile Ser Ser Lys Ala Met Gly Ile Met Asn
    50                  55                  60

Ser Phe Val Asn Asp Ile Phe Glu Arg Ile Ala Gly Glu Ala Ser Arg
65                  70                  75                  80

Leu Ala His Tyr Asn Lys Arg Ser Thr Ile Thr Ser Arg Glu Ile Gln
                85                  90                  95

Thr Ala Val Arg Leu Leu Leu Pro Gly Glu Leu Ala Lys His Ala Val
            100                 105                 110

Ser Glu Gly Thr Lys Ala Val Thr Lys Tyr Thr Ser Ser Lys
        115                 120                 125

<210> SEQ ID NO 32
<211> LENGTH: 7
<212> TYPE: PRT
<213> ORGANISM: Artificial Sequence
<220> FEATURE:
<223> OTHER INFORMATION: amino acid sequence 94-100 of SEQ ID NO: 31

<400> SEQUENCE: 32

Glu Ile Gln Thr Ala Val Arg
1               5

<210> SEQ ID NO 33
<211> LENGTH: 9
<212> TYPE: PRT
<213> ORGANISM: Artificial Sequence
<220> FEATURE:
<223> OTHER INFORMATION: amino acid sequence 101-109 of SEQ ID NO: 31

<400> SEQUENCE: 33

Leu Leu Leu Pro Gly Glu Leu Ala Lys
1               5

<210> SEQ ID NO 34
<211> LENGTH: 193
<212> TYPE: PRT
<213> ORGANISM: Homo sapiens
<220> FEATURE:
<221> NAME/KEY: MISC_FEATURE
<222> LOCATION: (1)..(193)
<223> OTHER INFORMATION: amino acid sequence of human histone H2B,
     uniprot ID Q6DN03.3, initial methionine not included

<400> SEQUENCE: 34

Met Pro Glu Pro Ala Lys Phe Ala Pro Ala Pro Lys Lys Gly Ser Lys
1               5                   10                  15

Lys Ala Val Thr Lys Ala Gln Lys Lys Asp Gly Lys Lys Arg Lys Arg
            20                  25                  30

Ser Arg Lys Glu Ser Tyr Ser Ile Tyr Val Tyr Lys Val Leu Lys Arg
        35                  40                  45

Val His Pro Asp Thr Gly Ile Trp Cys Lys Ala Met Gly Ile Met Asn
    50                  55                  60

```
Ser Phe Leu Asn Asp Ile Phe Glu Arg Ile Ala Gly Glu Ala Ser Arg
 65                  70                  75                  80

Leu Ala His Tyr Asn Lys Arg Ser Thr Ile Thr Ser Arg Arg Ser Arg
                 85                  90                  95

Arg Pro Cys Ala Cys Cys Cys Pro Ala Ser Trp Pro Thr Pro Cys
            100                 105                 110

Pro Arg Ala Pro Arg Arg Ser Pro Ser Thr Pro Ala Pro Ser Glu Ser
            115                 120                 125

Leu Pro Gly Pro Gly Ala Arg Ser Leu Pro Pro Ser Leu Pro Pro Arg
        130                 135                 140

Val Ala Gly Cys Phe Val Ser Lys Gly Ser Phe Gln Gly His Leu Thr
145                 150                 155                 160

Thr Ser Val Lys Glu Ser Phe Leu Cys Cys Gln Ser Gln Leu Met Phe
                165                 170                 175

Leu Ala Ser Arg Leu Val Asn Phe Arg Arg Ala His Asn Thr Lys His
            180                 185                 190

Arg
```

```
<210> SEQ ID NO 35
<211> LENGTH: 13
<212> TYPE: PRT
<213> ORGANISM: Artificial Sequence
<220> FEATURE:
<223> OTHER INFORMATION: amino acid sequence 181-193 of SEQ ID NO: 34

<400> SEQUENCE: 35

Leu Val Asn Phe Arg Arg Ala His Asn Thr Lys His Arg
1               5                   10
```

```
<210> SEQ ID NO 36
<211> LENGTH: 135
<212> TYPE: PRT
<213> ORGANISM: Homo sapiens
<220> FEATURE:
<221> NAME/KEY: MISC_FEATURE
<222> LOCATION: (1)..(135)
<223> OTHER INFORMATION: amino acid sequence of human histone H3.1 ,
      uniprot ID P68431.2, initial methionine not included

<400> SEQUENCE: 36

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ala Thr
            20                  25                  30

Gly Gly Val Lys Lys Pro His Arg Tyr Arg Pro Gly Thr Val Ala Leu
        35                  40                  45

Arg Glu Ile Arg Arg Tyr Gln Lys Ser Thr Glu Leu Leu Ile Arg Lys
    50                  55                  60

Leu Pro Phe Gln Arg Leu Val Arg Glu Ile Ala Gln Asp Phe Lys Thr
65                  70                  75                  80

Asp Leu Arg Phe Gln Ser Ser Ala Val Met Ala Leu Gln Glu Ala Cys
                85                  90                  95

Glu Ala Tyr Leu Val Gly Leu Phe Glu Asp Thr Asn Leu Cys Ala Ile
            100                 105                 110

His Ala Lys Arg Val Thr Ile Met Pro Lys Asp Ile Gln Leu Ala Arg
        115                 120                 125

Arg Ile Arg Gly Glu Arg Ala
    130                 135
```

<210> SEQ ID NO 37
<211> LENGTH: 7
<212> TYPE: PRT
<213> ORGANISM: Artificial Sequence
<220> FEATURE:
<223> OTHER INFORMATION: amino acid sequence 57-63 of SEQ ID NO: 36

<400> SEQUENCE: 37

Ser Thr Glu Leu Leu Ile Arg
1               5

<210> SEQ ID NO 38
<211> LENGTH: 6
<212> TYPE: PRT
<213> ORGANISM: Artificial Sequence
<220> FEATURE:
<223> OTHER INFORMATION: amino acid sequence 117-122 of SEQ ID NO: 36

<400> SEQUENCE: 38

Val Thr Ile Met Pro Lys
1               5

<210> SEQ ID NO 39
<211> LENGTH: 9
<212> TYPE: PRT
<213> ORGANISM: Artificial Sequence
<220> FEATURE:
<223> OTHER INFORMATION: amino acid sequence 41-49 of SEQ ID NO: 36

<400> SEQUENCE: 39

Tyr Arg Pro Gly Thr Val Ala Leu Arg
1               5

<210> SEQ ID NO 40
<211> LENGTH: 129
<212> TYPE: PRT
<213> ORGANISM: Homo sapiens
<220> FEATURE:
<221> NAME/KEY: MISC_FEATURE
<222> LOCATION: (1)..(129)
<223> OTHER INFORMATION: amino acid sequence of human histone H2A type
      3, uniprot ID Q7L7L0.3, initial methionine not included), Sigma
      recombinant H2A SRP0406

<400> SEQUENCE: 40

Ser Gly Arg Gly Lys Gln Gly Gly Lys Ala Arg Ala Lys Ala Lys Ser
1               5                   10                  15

Arg Ser Ser Arg Ala Gly Leu Gln Phe Pro Val Gly Arg Val His Arg
            20                  25                  30

Leu Leu Arg Lys Gly Asn Tyr Ser Glu Arg Val Gly Ala Gly Ala Pro
        35                  40                  45

Val Tyr Leu Ala Ala Val Leu Glu Tyr Leu Thr Ala Glu Ile Leu Glu
    50                  55                  60

Leu Ala Gly Asn Ala Ala Arg Asp Asn Lys Thr Arg Ile Ile Pro
65                  70                  75                  80

Arg His Leu Gln Leu Ala Ile Arg Asn Asp Glu Glu Leu Asn Lys Leu
                85                  90                  95

Leu Gly Arg Val Thr Ile Ala Gln Gly Gly Val Leu Pro Asn Ile Gln
            100                 105                 110

Ala Val Leu Leu Pro Lys Lys Thr Glu Ser His His Lys Ala Lys Gly
        115                 120                 125

Lys

```
<210> SEQ ID NO 41
<211> LENGTH: 193
<212> TYPE: PRT
<213> ORGANISM: Homo sapiens
<220> FEATURE:
<221> NAME/KEY: MISC_FEATURE
<222> LOCATION: (1)..(193)
<223> OTHER INFORMATION: amino acid sequence of human histone H1,
      uniprot ID P07305, initial methionine not included

<400> SEQUENCE: 41

Thr Glu Asn Ser Thr Ser Ala Pro Ala Ala Lys Pro Lys Arg Ala Lys
1               5                   10                  15

Ala Ser Lys Lys Ser Thr Asp His Pro Lys Tyr Ser Asp Met Ile Val
            20                  25                  30

Ala Ala Ile Gln Ala Glu Lys Asn Arg Ala Gly Ser Ser Arg Gln Ser
        35                  40                  45

Ile Gln Lys Tyr Ile Lys Ser His Tyr Lys Val Gly Glu Asn Ala Asp
    50                  55                  60

Ser Gln Ile Lys Leu Ser Ile Lys Arg Leu Val Thr Thr Gly Val Leu
65                  70                  75                  80

Lys Gln Thr Lys Gly Val Gly Ala Ser Gly Ser Phe Arg Leu Ala Lys
                85                  90                  95

Ser Asp Glu Pro Lys Lys Ser Val Ala Phe Lys Lys Thr Lys Lys Glu
            100                 105                 110

Ile Lys Lys Val Ala Thr Pro Lys Lys Ala Ser Lys Pro Lys Lys Ala
            115                 120                 125

Ala Ser Lys Ala Pro Thr Lys Lys Pro Lys Ala Thr Pro Val Lys Lys
    130                 135                 140

Ala Lys Lys Lys Leu Ala Ala Thr Pro Lys Lys Ala Lys Lys Pro Lys
145                 150                 155                 160

Thr Val Lys Ala Lys Pro Val Lys Ala Ser Lys Pro Lys Lys Ala Lys
                165                 170                 175

Pro Val Lys Pro Lys Ala Lys Ser Ser Ala Lys Arg Ala Gly Lys Lys
            180                 185                 190

Lys
```